(12) United States Patent
Maher

(10) Patent No.: US 11,680,261 B2
(45) Date of Patent: Jun. 20, 2023

(54) NEEDLE-BASED DEVICES AND METHODS FOR IN VIVO DIAGNOSTICS OF DISEASE CONDITIONS

(71) Applicant: GRAIL, LLC, Menlo Park, CA (US)

(72) Inventor: M. Cyrus Maher, San Mateo, CA (US)

(73) Assignee: GRAIL, INC., Menlo Park, CA (US)

( * ) Notice: Subject to any disclaimer, the term of this patent is extended or adjusted under 35 U.S.C. 154(b) by 724 days.

(21) Appl. No.: 16/685,334

(22) Filed: Nov. 15, 2019

(65) Prior Publication Data

US 2020/0181609 A1 Jun. 11, 2020

Related U.S. Application Data

(60) Provisional application No. 62/767,813, filed on Nov. 15, 2018.

(51) Int. Cl.
| | | |
|---|---|---|
| *C12N 9/22* | (2006.01) | |
| *A61B 5/15* | (2006.01) | |
| *C12Q 1/6827* | (2018.01) | |
| *C12Q 1/6883* | (2018.01) | |
| *C12Q 1/6886* | (2018.01) | |
| *C12N 15/11* | (2006.01) | |
| *C12Q 1/6816* | (2018.01) | |
| *G01N 33/574* | (2006.01) | |
| *A61B 5/157* | (2006.01) | |
| *G01N 21/64* | (2006.01) | |

(52) U.S. Cl.
CPC .......... *C12N 15/11* (2013.01); *A61B 5/15003* (2013.01); *A61B 5/150206* (2013.01); *C12N 9/22* (2013.01); *C12Q 1/6816* (2013.01); *G01N 33/574* (2013.01); *A61B 5/157* (2013.01); *C12N 2310/20* (2017.05); *C12N 2800/80* (2013.01); *C12Q 1/6827* (2013.01); *C12Q 1/6883* (2013.01); *C12Q 1/6886* (2013.01); *C12Q 2563/107* (2013.01); *G01N 21/6486* (2013.01)

(58) Field of Classification Search
CPC ............................ A61B 5/157; A61B 5/15003
See application file for complete search history.

(56) References Cited

U.S. PATENT DOCUMENTS

| 4,683,195 A | 7/1987 | Mullis et al. |
| 6,818,395 B1 | 11/2004 | Quake et al. |

(Continued)

FOREIGN PATENT DOCUMENTS

| CN | 101679959 | 3/2010 |
| EP | 2 963 113 A1 | 1/2016 |

(Continued)

OTHER PUBLICATIONS

Tseng et al. Journal of Thoracic Oncology. 2015. 10(4):603-610. (Year: 2015).*

(Continued)

*Primary Examiner* — Joseph G. Dauner
(74) *Attorney, Agent, or Firm* — Benjamin C. Pelletier; Vincent K. Shier; Haynes and Boone, LLP

(57) ABSTRACT

Diagnostic devices and methods are provided for screening for a disease condition, including a cancer condition or a mendelian disease. The diagnostic devices allow for in vivo contact of cell-free nucleic acids or circulating tumor cells. The diagnostic device has a needle with a body and a detection reaction module attached to the body.

21 Claims, 2 Drawing Sheets

(56) References Cited

U.S. PATENT DOCUMENTS

| | | | |
|---|---|---|---|
| 7,169,560 | B2 | 1/2007 | Lapidus et al. |
| 7,282,337 | B1 | 10/2007 | Harris et al. |
| 7,666,593 | B2 | 2/2010 | Lapidus |
| 2002/0164629 | A1 | 11/2002 | Quake et al. |
| 2009/0026082 | A1 | 1/2009 | Rothberg et al. |
| 2009/0127589 | A1 | 5/2009 | Rothberg et al. |
| 2009/0156412 | A1 | 6/2009 | Harris et al. |
| 2009/0191565 | A1 | 7/2009 | Lapidus et al. |
| 2010/0035252 | A1 | 2/2010 | Rothberg et al. |
| 2010/0086533 | A1 | 4/2010 | Montoya et al. |
| 2010/0137143 | A1 | 6/2010 | Rothberg et al. |
| 2010/0188073 | A1 | 7/2010 | Rothberg et al. |
| 2010/0197507 | A1 | 8/2010 | Rothberg et al. |
| 2010/0282617 | A1 | 11/2010 | Rothberg et al. |
| 2010/0300559 | A1 | 12/2010 | Schultz et al. |
| 2010/0300895 | A1 | 12/2010 | Nobile et al. |
| 2010/0301398 | A1 | 12/2010 | Rothberg et al. |
| 2010/0304982 | A1 | 12/2010 | Hinz et al. |
| 2014/0356867 | A1 | 12/2014 | Jon et al. |
| 2016/0017396 | A1 | 1/2016 | Cann et al. |

FOREIGN PATENT DOCUMENTS

| | | | |
|---|---|---|---|
| WO | WO 2000/070039 A1 | | 11/2000 |
| WO | WO 2013/191775 A2 | | 12/2013 |
| WO | WO 2015/075056 A1 | | 5/2015 |
| WO | WO 2015/116686 A1 | | 8/2015 |
| WO | WO 2016/014409 A1 | | 1/2016 |
| WO | WO 2016/077350 A1 | | 5/2016 |
| WO | WO 2016/186946 A1 | | 11/2016 |
| WO | WO-2017185086 A1 | * | 10/2017 |

OTHER PUBLICATIONS

Bettegowda, et al., "Detection of circulating tumor DNA in early- and late-stage human malignancies," SciTrans Med, vol. 6. No. 224, pp. 1-11, 2014.

Braslavsky, et al., "Sequence information can be obtained from single DNA molecules," PNAS, vol. 100, No. 7, pp. 3960-3964, 2003.

Anders, et al., "Structural Plasticity of PAM Recognition by Engineered Variants of the RNA-Guided Endoculease Cas9," Molecular Cell, vol. 61, No. 6, pp. 895-902, Mar. 17, 2016.

Courtney, et al., "CRISPR/Cas9 DNA cleavage at SNP-derived PAM enables both in vitro and in vivo KRT12 mutation-specific targeting," Gene Therapy, vol. 23, No. 1, pp. 108-112, Aug. 20, 2015.

Duncavage, et al., "Hybrid Capture and Next-Generation Sequencing Identify Viral Integration Sites from Formalin-Fixed, Paraffin-Embedded Tissue," J Mol Diagn., vol. 13, No. 3, pp. 325-333, 2011.

Harris, et al., "Single-Molecule DNA Sequencing of a Viral Genome," Science, vol. 320, pp. 106-109, 2008.

Khurana, Ekta, et al., "Role of non-coding sequence variants in cancer," Nature Reviews Genetics, vol. 17, No. 2, pp. 93-108, Feb. 2016.

Kleinstiver, et al., "Broadening the targeting range of *Staphylococcus aureus* CRISPR-Cas9 by modifying PAM recognition," Nature Biotechnology, vol. 33, No. 12, pp. 1293-1298, Dec. 1, 2015.

Kleinstiver, et al., "Engineered CRISPR-Cas9 nucleases with altered PAM specificities," Nature, vol. 523, No. 7561, pp. 481-485, Jun. 22, 2015.

Marguiles, et al., "Genome sequencing in microfabricated high-density picolitre reactors," Nature 437(7057), pp. 376-380, 2005.

Maxam, et al., "A new method for sequencing DNA," PNAS, vol. 74, No. 2, pp. 560-564, 1977.

Moudrianakis, et al., "Base Sequence Determination In Nucleic Acids With The Electron Microscope III. chemistry and microscopy of guanine-labeled DNA," PNAS, vol. 53, No. 3, pp. 564-671, 1965.

Mouliere, et al., "Circulating tumor-derived DNA is shorter than somatic DNA in plasma," PNAS, vol. 112, No. 11, pp. 3178-3179, 2015.

Mouliere, et al., "Multi-marker Analysis of Circulating Cell-free DNA Toward Personalized Medicine for Colorectal Cancer," Mol Oncol., vol. 8, No. 5, pp. 927-947, Mar. 2014.

Newman, et al., "An ultrasensitive method for quantitating circulating tumor DNA with broad patient coverage," Nat Med, vol. 20, No. 5, pp. 548-554, 2014.

Sanger, et al., "DNA sequencing with chain-terminating inhibitors," PNAS, vol. 74, No. 12, pp. 5463-5467, 1977.

Shin, et al., "Permanent inactivation of Huntington's disease mutation by personalized allele-specific CRISPR/Cas9," Human Molecular Genetics, ddw286, Sep. 15, 2016.

Soni, et al., "Progress toward ultrafast DNA sequencing using solid-state nanopores," Clin. Chem, 53(11), pp. 1996-2001, 2007.

\* cited by examiner

NEEDLE-BASED DEVICES AND METHODS FOR IN VIVO DIAGNOSTICS OF DISEASE CONDITIONS

CROSS REFERENCE TO RELATED APPLICATION

This application claims priority to U.S. Provisional Patent Application No. 62/767,813, filed Nov. 15, 2018, the contents of which is hereby incorporated by reference.

FIELD OF THE INVENTION

The disclosed implementations relate generally to improved devices and methods for in vivo diagnosis and/or prognosis of a disease condition in a human patient.

BACKGROUND OF THE INVENTION

The increasing knowledge of the molecular basis for cancer and the rapid development of next generation sequencing techniques are advancing the study of early molecular alterations involved in cancer development in body fluids. Specific genetic and epigenetic alterations associated with such cancer development are found in plasma, serum, and urine cell-free DNA (cfDNA). Such alterations could potentially be used as diagnostic biomarkers for several types of cancers. See Salvi et al., 2016, "Cell-free DNA as a diagnostic marker for cancer: current insights," *Onco Targets Ther.* 9:6549-6559.

With a total of over 1.6 million new cases each year in the United States as of 2017, cancer represents a prominent worldwide public health problem. See, Siegel et al., 2017, "Cancer statistics," *CA Cancer J Clin.* 67(1):7-30. Screening programs and early diagnosis have an important impact in improving disease-free survival and reducing mortality in cancer patients. As noninvasive approaches for early diagnosis foster patient compliance, they can be included in screening programs.

Cell-free DNA (cfDNA) can be found in serum, plasma, urine, and other body fluids (Chan et al., "Clinical Sciences Reviews Committee of the Association of Clinical Biochemists Cell-free nucleic acids in plasma, serum and urine: a new tool in molecular diagnosis," *Ann Clin Biochem.* 2003; 40(Pt 2):122-130) representing a "liquid biopsy," which is a circulating picture of a specific disease. See, De Mattos-Arruda and Caldas, 2016, "Cell-free circulating tumour DNA as a liquid biopsy in breast cancer," *Mol Oncol.* 2016; 10(3):464-474. This represents a potential, non-invasive method of screening for a variety of cancers.

The existence of cfDNA was demonstrated by Mandel and Metais (Mandel and Metais), "P. Les acides nucleiques du plasma sanguin chez 1' homme [The nucleic acids in blood plasma in humans]," *C R Seances Soc Biol Fil.* 1948; 142(3-4):241-243). cfDNA originates from necrotic or apoptotic cells, and it is generally released by all types of cells. Stroun et al further showed that specific cancer alterations could be found in the cfDNA of patients. See, Stroun et al., "Neoplastic characteristics of the DNA found in the plasma of cancer patients," *Oncology.* 1989; 46(5):318-322). A number of following papers confirmed that cfDNA contains specific tumor-related alterations, such as mutations, methylation, and copy number variations (CNVs), thus confirming the existence of circulating tumor DNA (ctDNA). See, Goessl et al., "Fluorescent methylation-specific polymerase chain reaction for DNA-based detection of prostate cancer in bodily fluids," *Cancer Res.* 2000; 60(21):5941-5945 and Frenel et al., 2015, "Serial next-generation sequencing of circulating cell-free DNA evaluating tumor clone response to molecularly targeted drug administration. *Clin Cancer Res.* 21(20):4586-4596. It is believed that the cell-free nucleic acids are derived from a combination of apoptosis, necrosis, and active release from cancer cells.

Circulating tumor cells (CTCs) are rare cells that are released from a tumor into the bloodstream. A single CTC can exist in a patient among millions or more blood cells. The cells are undetectable in patients when using conventional histopathology methods.

Early detection of cell-free nucleic acids and CTCs could provide valuable information to a clinician when assessing the disease stage and devising an effective therapy. Unfortunately, the ability to diagnose cancer from blood is inherently limited by the volume of blood that must be drawn to detect circulating cell-free nucleic acids and CTCs. Currently, only 0.1% of the blood in the body is sampled to detect cancer, thus leading to missed diagnoses when tumor fractions are low.

Isolating and characterizing circulating cell-free nucleic acids and circulating tumor cells directly in a patient's blood stream may be useful for detecting early stage cancers and monitoring their progression. As such, there is a need for novel methods and devices for in vivo detection of cancer.

SUMMARY OF THE INVENTION

The present disclosure provides devices and methods for in vivo isolating and detecting circulating cell-free nucleic acids or circulating tumor cells in subjects to identify a cancer condition in subjects as needed in the art.

1. Devices and Methods for Circulating Cell-Free Nucleic Acids

One aspect of the present disclosure provides a diagnostic device comprising: comprising a needle having a body comprising a plurality of sample reaction nanostructures disposed on a surface of the body, wherein the respective sample reaction nanostructures of the plurality of sample reaction nanostructures collectively form an array comprising a plurality of elements; each respective element of the array is at a spatially addressable position on the surface of the body; each respective element of the array is populated with a sample reaction nanostructure in the plurality of sample reaction nanostructures. In some embodiments, each sample reaction nanostructure in the plurality of sample reaction nanostructures comprises at least one Cas protein and at least one target engineered CRISPR targeting RNA (crRNA) at the corresponding addressable position on the surface of the body. In some embodiments, the sample reaction nanostructure further comprises at least one non-specific nucleic acid reporter comprising (i) a nucleic acid cleavable by the at least one Cas protein and (ii) a fluorophore pair comprising a quencher molecule and a fluorophore, wherein the fluorophore is detectable upon cleavage of the at least one non-specific nucleic acid reporter. In some instances, the at least one Cas protein is selected from the group consisting of Cas12a, Cas13, Csm6, a derivative thereof, and a variant thereof.

In some embodiments, the device has a detection limit of at least 200 zM.

In some embodiments, the plurality of sample reaction nanostructures detects the presence of one or more targets selected from the group consisting of one or more mutations in one or more of the genes TP53, PIK3CA, PTEN, APC, VHL, KRAS, MLL3, MLL2, ARID1A, PBRM1, NAV3, EGFR, NF1, PIK3R1, CDKN2A, GATA3, RB1, NOTCH1, FBXW7, CTNNB1, DNMT3A, MAP3K1, FLT3, MALAT1, TSHZ3, KEAP1, CDH1, ARHGAP35, CTCF, NFE2L2, SETBP1, BAP1, NPM1, RUNX1, NRAS, IDH1, TBX3, MAP2K4, RPL22, STK11, CRIPAK, CEBPA, KDM6A, EPHA3, AKT1, STAG2, BRAF, AR, AJUBA, EPPK1, TSHZ2, PIK3CG, SOX9, ATM, CDKN1B, WT1, HGF, KDM5C, PRX, ERBB4, MTOR, TLR4, U2AF1, ARID5B, TET2, ATRX, MLL4, ELF3, BRCA1, LRRK2, POLQ, FOXA1, IDH2, CHEK2, KIT, HIST1H1C, SETD2, PDGFRA, EP300, FGFR2, CCND1, EPHB6, SMAD4, FOXA2, USP9X, BRCA2, NFE2L3, FGFR3, ASXL1, TGFBR2, SOX17, CDKN1A, B4GALT3, SF3B1, TAF1, PPP2R1A, CBFB, ATR, SIN3A, VEZF1, HIST1H2BD, EIF4A2, CDK12, PHF6, SMC1A, PTPN11, ACVR1B, MAPK8IP1, H3F3C, NSD1, TBL1XR1, EGR3, ACVR2A, MECOM, LIFR, SMC3, NCOR1, RPL5, SMAD2, SPOP, AXIN2, MIR142, RAD21, ERCC2, CDKN2C, EZH2, and PCBP1.

The plurality of sample reaction nanostructures may comprise 100 nanostructures. In some embodiments, the plurality of sample reaction nanostructures comprises 1000 nanostructures. In some embodiments, the plurality of sample reaction nanostructures comprises from 50 to 2000 nanostructures.

In some embodiments, the surface of the body comprises a non-corrosive metal, a non-corrosive alloy, nanoparticles, an element, a polymer, gold, platinum, an alloy, or a combination thereof. In some instances, the body is made of steel and the surface comprises a deposit layer on the body under conditions that cause an average thickness of the layer to be 50 Angstroms or less. In other instances, the body is made of steel and the surface comprises a deposit layer on the body under conditions that cause an average thickness of the layer to be 40 Angstroms or less or 20 Angstroms or less.

In some embodiments, the average thickness of the deposit layer is 1 Angstroms to 50 Angstroms. In other embodiments, the average thickness of the deposit layer is 1 Angstroms to 25 Angstroms. In certain embodiments, the average thickness of the deposit layer is 1 Angstroms to 15 Angstroms. In particular embodiments, the average thickness of the deposit layer is 1 Angstroms to 10 Angstroms.

In some embodiments, the length of the body is between about 10 mm and about 200 mm. In some embodiments, the body has an inner diameter of at least 2 µm. In some embodiments, the plurality of sample reaction nanostructures is formed at the corresponding addressable position on the surface of the body by lithography.

In some embodiments, the plurality of sample reaction nanostructures contacts a cell-free biological sample in vivo. In some embodiments, the cell-free biological sample comprises cell-free nucleic acid. In certain embodiments, the cell-free biological sample comprises cell-free DNA (cfDNA) molecules. In particular embodiments, the cell-free biological sample comprises cell-free RNA (cfRNA) molecules.

In some embodiments, the device further comprises an enrichment module comprising a binding molecule that binds the cell-free biological sample prior to the cell-free biological sample contacting the plurality of sample reaction nanostructures, wherein the enrichment module is in fluid contact with the plurality of sample reaction nanostructures.

In some aspects, provided herein is a method of fabricating the diagnostic device described herein comprising using lithography to dispose the plurality of sample reaction nanostructures on the surface of the body.

In another aspect, provided herein is a method of screening for a disease condition in a subject using a diagnostic device comprising a needle having a body, wherein a plurality of sample reaction nanostructures is disposed on a surface of the body for contacting a cell-free biological sample in vivo. The method comprises: (a) inserting the diagnostic device into the bloodstream of the subject such that the cell-free biological sample contacts the plurality of sample reaction nanostructures; (b) removing the diagnostic device from the subject after a period of time; and (c) analyzing the plurality of sample reaction nanostructures for a signal that is indicative of the disease condition. In some embodiments, the analyzing of step (c) comprises detecting comprising subjecting the device to a spectrophotometer. In some embodiments, the period of time is for about 1 minute to about 15 minutes.

In yet another aspect, provided herein is a method of predicting the likelihood of a subject having a disease condition to respond to a therapy using a prognostic device comprising a needle having a body, wherein a plurality of sample reaction nanostructures is disposed on a surface of the body for contacting with a cell-free biological sample in vivo. The predictive method comprises: (a) inserting the prognostic device into the bloodstream of the subject such that the cell-free biological sample contacts the plurality of sample reaction nanostructures; (b) removing the prognostic device from the subject after a period of time; and (c) analyzing the plurality of sample reaction nanostructures for a signal that is indicative of the predicted likelihood of the subject to respond to the therapy. In some embodiments, the analyzing of step (c) comprises detecting comprising subjecting the device to a spectrophotometer. In some embodiments, the period of time is for about 1 minute to about 15 minutes.

In some embodiments, the disease condition is a cancer condition. In other embodiments, the disease condition is a mendelian disease.

In some embodiments, the cancer condition is breast cancer, lung cancer, prostate cancer, colorectal cancer, renal cancer, uterine cancer, pancreatic cancer, cancer of the esophagus, a lymphoma, head/neck cancer, ovarian cancer, a hepatobiliary cancer, a melanoma, cervical cancer, multiple myeloma, leukemia, thyroid cancer, bladder cancer, gastric cancer, or a combination thereof. In particular embodiments, the cancer condition is a predefined stage of a breast cancer, a predefined stage of a lung cancer, a predefined stage of a prostate cancer, a predefined stage of a colorectal cancer, a predefined stage of a renal cancer, a predefined stage of a uterine cancer, a predefined stage of a pancreatic cancer, a predefined stage of a cancer of the esophagus, a predefined stage of a lymphoma, a predefined stage of a head/neck cancer, a predefined stage of a ovarian cancer, a predefined stage of a hepatobiliary cancer, a predefined stage of a melanoma, a predefined stage of a cervical cancer, a predefined stage of a multiple myeloma, a predefined stage of a leukemia, a predefined stage of a thyroid cancer, a predefined stage of a bladder cancer, or a predefined stage of a gastric cancer. In some instances, the cancer condition is a predefined subtype of a cancer. In certain instances, the cancer condition is early stage cancer. In other instances, the cancer condition is late stage cancer.

As described above, the diagnostic or prognostic device comprises a needle having a body, wherein a plurality of sample reaction nanostructures. In some embodiments, the respective sample reaction nanostructures of the plurality of sample reaction nanostructures collectively form an array comprising a plurality of elements; each respective element of the array is at a spatially addressable position on the surface of the body; each respective element of the array is populated with a sample reaction nanostructure in the plurality of sample reaction nanostructures. In some embodiments, each sample reaction nanostructure in the plurality of sample reaction nanostructures comprises at least one Cas protein and at least one target engineered CRISPR targeting RNA (crRNA) that is formed at the corresponding addressable position on the surface of the body.

In some embodiments, the sample reaction nanostructure also comprises: at least one non-specific nucleic acid reporter comprising (i) a nucleic acid cleavable by the at least one Cas protein and (ii) a fluorescence resonance transfer pair comprising a quencher molecule and a fluorophore, wherein the fluorophore is detectable upon cleavage of the at least one non-specific nucleic acid reporter. In some instances, the at least one Cas protein is selected from the group consisting of Cas12a, Cas13, Csm6, a derivative thereof, and a variant thereof.

In some embodiments, the cell-free biological sample comprises cell-free nucleic acid molecules. In certain embodiments, the cell-free biological sample comprises cell-free DNA (cfDNA) molecules. In particular embodiments, the cell-free biological sample comprises cell-free RNA (cfRNA) molecules.

In some embodiments, the plurality of sample reaction nanostructures detects the presence of one or more targets selected from the group consisting of one or more mutations in one or more of the genes that include but are not limited to P53, PIK3CA, MAP3K1, MAP2K4, PIK3R1, LPA, KRAS, ERBB2, FGFR2, and TNXB.

In one embodiment, the plurality of sample reaction nanostructures comprises 100 nanostructures. In some embodiments, the plurality of sample reaction nanostructures comprises 1000 nanostructures. In some embodiments, the plurality of sample reaction nanostructures comprises from 50 to 2000 nanostructures. In some embodiments, the diagnostic or prognostic device has a detection limit of at least 200 zM.

In some embodiments, the surface of the body comprises a non-corrosive metal, a non-corrosive alloy, nanoparticles, an element, a polymer, gold, platinum, an alloy, carbon, titanium dioxide, aluminum oxide, or a combination thereof. In some instances, the body is made of steel and the surface comprises a deposit layer on the body under conditions that cause an average thickness of the layer to be 40 Angstroms or less. In other instances, the body is made of steel and the surface comprises a deposit layer on the body under conditions that cause an average thickness of the layer to be 20 Angstroms or less. In some embodiments, the average thickness of the deposit layer is 1 Angstroms to 50 Angstroms. In other embodiments, the average thickness of the deposit layer is 1 Angstroms to 25 Angstroms. In certain embodiments, the average thickness of the deposit layer is 1 Angstroms to 15 Angstroms. In particular embodiments, the average thickness of the deposit layer is 1 Angstroms to 10 Angstroms. In some embodiments, the length of the body is between about 10 mm and about 200 mm. In certain embodiments, the body has an inner diameter of at least 2 μm.

In some embodiments, the device further comprises an enrichment module comprising a binding molecule that binds the cell-free biological sample prior to the cell-free biological sample contacting the plurality of sample reaction nanostructures, wherein the enrichment module is in fluid contact with the plurality of sample reaction nanostructures.

In some embodiments, the sample reaction nanostructure of the needle body is formed by lithography.

2. Devices and Methods for Circulating Tumor Cells

One aspect of the present disclosure provides a diagnostic device comprising a needle having a body comprising a plurality of sample reaction nanostructures disposed on a surface of the body, wherein said plurality of sample reaction nanostructures contact a biological sample in vivo, and wherein each sample reaction nanostructure of the plurality of sample reaction nanostructures comprises at least one antibody targeting a circulating tumor cell (CTC).

In some embodiments, the respective sample reaction nanostructures of the plurality of sample reaction nanostructures collectively form an array comprising a plurality of elements; each respective element of the array is at a spatially addressable position on the surface of the body; each respective element of the array is populated with a sample reaction nanostructure in the plurality of sample reaction nanostructures; and the at least one antibody targeting a CTC is deposited at the corresponding addressable position on the surface of the body. The antibody can be deposited by any known method, such as but not limited to, lithography. In some embodiments, the at least one antibody binds a first target molecule on the surface of the CTC. In some embodiments, the first target molecule is selected from the group consisting of EPCAM, PSMA, and HER2.

In some embodiments, each sample reaction nanostructure also comprises an antibody reporter comprising (i) an antibody that binds a second target molecule on the surface of the CTC and (ii) a reporter molecule, wherein the first and second target molecules are different. The second target molecule may be selected from the group consisting of EPCAM, PSMA, and HER2. In various embodiments, the reporter molecule comprises a detectable moiety. In some embodiments, the reporter molecule comprises a detecting antibody attached to the detectable moiety, wherein the detecting antibody binds the antibody of the antibody reporter.

In some embodiments, the method further relies on comprising an enrichment module attached to the body, the enrichment module comprising a binding molecule that binds the CTC prior to the CTC contacting the plurality of sample reaction nanostructures. In other embodiments, the method further relies on comprising an enrichment module attached to the body, the enrichment module comprising a size filtration membrane to isolate the CTC prior to the CTC contacting the plurality of sample reaction nanostructures.

In some embodiments, the surface of the body comprises a non-corrosive metal, a non-corrosive alloy, nanoparticles, an element, a polymer, gold, platinum, an alloy, carbon, titanium dioxide, aluminum oxide, or a combination thereof. In some instances, the body is made of steel and the surface comprises a deposit layer on the body under conditions that cause an average thickness of the layer to be 40 Angstroms or less. In other instances, the body is made of steel and the surface comprises a deposit layer on the body under conditions that cause an average thickness of the layer to be 20 Angstroms or less. In some embodiments, the average thickness of the deposit layer is 1 Angstroms to 50 Angstroms. In other embodiments, the average thickness of the deposit layer is 1 Angstroms to 25 Angstroms. In certain embodiments, the average thickness of the deposit layer is 1 Angstroms to 15 Angstroms. In particular embodiments, the average thickness of the deposit layer is 1 Angstroms to 10 Angstroms. In some embodiments, the length of the body is between about 10 mm and about 200 mm. In certain embodiments, the body of the needle has an inner diameter of at least 1 μm. In other embodiments, the body has an inner diameter of at least 4 μm. In some embodiments, the plurality of sample reaction nanostructures may comprise 100 nanostructures. In some embodiments, the plurality of sample reaction nanostructures comprises 1000 nanostructures. In some embodiments, the plurality of sample reaction nanostructures comprises from 50 to 2000 nanostructures.

Provided herein is a method of fabricating the diagnostic device for CTCs comprising using lithography to dispose the plurality of sample reaction nanostructures on the surface of the body of the needle.

In another aspect, provided herein is a method of screening for a cancer condition in a subject using a diagnostic device comprising a needle having a body, wherein a plurality of sample reaction nanostructures is disposed on a surface of the body for contacting with a biological sample in vivo, wherein the device detects or captures a circulating tumor cell (CTC) or cancer-cell originated cell-free nucleic acids in the biological sample. In some embodiments, the device for detect or capture a circulating tumor cell (CTC) comprises sample reaction nanostructure comprising at least one antibody targeting the CTC. In various embodiments, the device for detect or capture cancer-cell originated cell-free nucleic acids comprises sample reaction nanostructure comprising at least one Cas protein and at least one target engineered CRISPR targeting RNA (crRNA).

The screening method comprises: (a) inserting the diagnostic device into the bloodstream of the subject such that the biological sample contacts the plurality of sample reaction nanostructures; and (b) removing the diagnostic device from the subject after a period of time; and (c) analyzing the plurality of sample reaction nanostructures for a signal that is indicative of the cancer condition. In one embodiments, analyzing comprises detecting comprising subjecting the device to a spectrophotometer. In other words, analyzing of step (c) comprises detecting a signal emitted from the device, wherein detection of the signal is indicative of the cancer condition.

In one aspect, provided herein is a method of predicting the likelihood of a subject having a cancer condition to respond to an anti-cancer therapy using a prognostic device comprising a needle having a body, wherein a plurality of sample reaction nanostructures is disposed on a surface of the body for contacting with a biological sample in vivo, wherein the biological sample comprises a circulating tumor cell (CTC). The predictive method comprises: (a) inserting the prognostic device into the bloodstream of the subject such that the biological sample contacts the plurality of sample reaction nanostructures; and (b) removing the prognostic device from the subject after a period of time; and (c) analyzing the plurality of sample reaction nanostructures for a signal that is indicative of the disease condition. In some embodiments, the analyzing comprises detecting comprising subjecting the device to a spectrophotometer. In some instances, analyzing of step (c) comprises detecting a signal emitted from the device, wherein detection of the signal is indicative of the predicted likelihood of the subject to response to the anti-cancer therapy. In some embodiments, the cancer condition of the methods described herein include breast cancer, lung cancer, prostate cancer, colorectal cancer, renal cancer, uterine cancer, pancreatic cancer, cancer of the esophagus, a lymphoma, head/neck cancer, ovarian cancer, a hepatobiliary cancer, a melanoma, cervical cancer, multiple myeloma, leukemia, thyroid cancer, bladder cancer, gastric cancer, or a combination thereof. In particular embodiments, the cancer condition is a predefined stage of a breast cancer, a predefined stage of a lung cancer, a predefined stage of a prostate cancer, a predefined stage of a colorectal cancer, a predefined stage of a renal cancer, a predefined stage of a uterine cancer, a predefined stage of a pancreatic cancer, a predefined stage of a cancer of the esophagus, a predefined stage of a lymphoma, a predefined stage of a head/neck cancer, a predefined stage of a ovarian cancer, a predefined stage of a hepatobiliary cancer, a predefined stage of a melanoma, a predefined stage of a cervical cancer, a predefined stage of a multiple myeloma, a predefined stage of a leukemia, a predefined stage of a thyroid cancer, a predefined stage of a bladder cancer, or a predefined stage of a gastric cancer. In some instances, the cancer condition is a predefined subtype of a cancer. In certain instances, the cancer condition is early stage cancer. In other instances, the cancer condition is late stage cancer.

As described above, the cancer diagnostic or prognostic device comprises a needle having a body, wherein a plurality of sample reaction nanostructures is disposed on a surface of the body for contacting with a biological sample in vivo. In some embodiments, the respective sample reaction nanostructures of the plurality of sample reaction nanostructures collectively form an array comprising a plurality of elements; each respective element of the array is at a spatially addressable position on the surface of the body; each respective element of the array is populated with a sample reaction nanostructure in the plurality of sample reaction nanostructures. In certain embodiments, each sample reaction nanostructure of the plurality of sample reaction nanostructures comprises at least one antibody targeting a circulating tumor cell (CTC).

In some embodiments, the at least one antibody binds a first target molecule on the surface of the CTC. In some embodiments, the first target molecule is selected from the group consisting of EPCAM, PSMA, and HER2. In some embodiments, the sample reaction nanostructure comprises an antibody reporter comprising (i) an antibody that binds a second target molecule on the surface of the CTC and (ii) a reporter molecule, wherein the first and second target molecules are different. the second target molecule may be selected from the group consisting of EPCAM, PSMA, and HER2. In various embodiments, the reporter molecule comprises a detectable moiety. In some embodiments, the reporter molecule comprises a detecting antibody attached to the detectable moiety, wherein the detecting antibody binds the antibody of the antibody reporter.

In some embodiments, the method further relies on comprising an enrichment module attached to the body, the enrichment module comprising a binding molecule that binds the CTC prior to the CTC contacting the plurality of sample reaction nanostructures. In other embodiments, the method further relies on comprising an enrichment module attached to the body, the enrichment module comprising a size filtration membrane to isolate the CTC prior to the CTC contacting the plurality of sample reaction nanostructures.

n some embodiments, the surface of the body comprises a non-corrosive metal, a non-corrosive alloy, nanoparticles, an element, a polymer, gold, platinum, an alloy, carbon, titanium dioxide, aluminum oxide, or a combination thereof. In some instances, the body is made of steel and the surface comprises a deposit layer on the body under conditions that cause an average thickness of the layer to be 40 Angstroms or less. In other instances, the body is made of steel and the surface comprises a deposit layer on the body under conditions that cause an average thickness of the layer to be 20 Angstroms or less. In some embodiments, the average thickness of the deposit layer is 1 Angstroms to 50 Angstroms. In other embodiments, the average thickness of the deposit layer is 1 Angstroms to 25 Angstroms. In certain embodiments, the average thickness of the deposit layer is 1

Angstroms to 15 Angstroms. In particular embodiments, the average thickness of the deposit layer is 1 Angstroms to 10 Angstroms. In certain embodiments, the body of the needle has an inner diameter of at least 1 µm. In other embodiments, the body has an inner diameter of at least 4 µm. In some embodiments, the plurality of sample reaction nanostructures may comprise 100 nanostructures. In some embodiments, the plurality of sample reaction nanostructures comprises 1000 nanostructures.

In another aspect, provided herein is a method of fabricating any of the diagnostic or prognostic devices described comprising using lithography to dispose the plurality of sample reaction nanostructures on the surface of the body.

It will be understood that, due to specific binding and subsequent enrichment of target molecules, devices and methods disclosed herein can be applied to detect any marker (protein or nucleic acid) representative of a disease condition.

The various innovations can be used in combination or separately. The foregoing and other objects, features, and advantages of the invention will become more apparent from the following detailed description.

BRIEF DESCRIPTION OF THE DRAWINGS

The implementations disclosed herein are illustrated by way of example, and not by way of limitation, in the figures of the accompanying drawings. Like reference numerals refer to corresponding parts throughout the drawings.

FIG. 1 depicts a portion of the addressable, patterned plurality of sample reaction nanostructures 106. The needle 104 can be attached to another component of the device via part 102.

DETAILED DESCRIPTION OF THE INVENTION

I. Introduction

Figure 1:
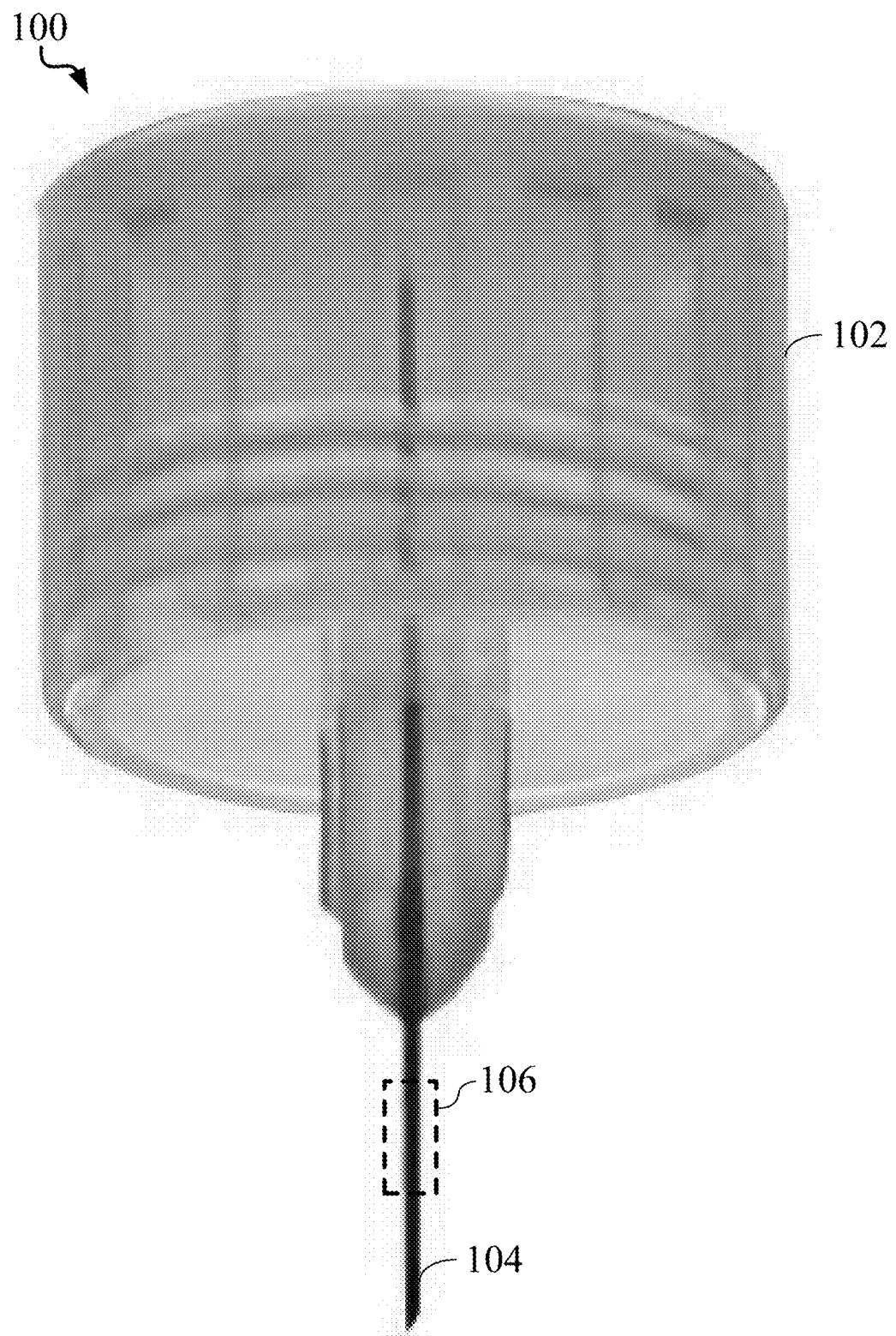
FIG. 1 shows an exemplary diagnostic device 100 described herein. The needle 104 has a body comprising a plurality of sample reaction nanostructures disposed on the surface of the body.

The in vivo diagnostic device described herein can be used as a portable, point-of-care medical tool for isolating and detecting circulating cell-free nucleic acid or circulating tumor cells in a patient suspected of having cancer. The methods employing the device enable rapid, repeatable, and reliable detection of disease conditions in a clinical setting.

II. In Vivo Diagnostic or Prognostic Devices

The device described herein is capable of detecting a plurality of multiple different target molecules present in the circulating peripheral blood of a subject such as a human subject having or suspected of having a disease condition. In some embodiments, the target molecules include circulating cell-free DNA and circulating cell-free RNA. In other embodiments, the target molecules include molecules on the cell surface of circulating tumor cells (CTCs). In some cases, the device is applied to a subject without extracting or harvesting a biological sample comprising the target molecules from the subject prior to detecting them.

As used herein, the terms "biological sample," "patient sample," and "sample" are interchangeably used and refer to any sample taken from a subject, which can reflect a biological state associated with the subject. In some embodiments such samples contain cell-free nucleic acids such as cell-free DNA. In some embodiments, such samples include nucleic acids other than or in addition to cell-free nucleic acids. Examples of biological samples include, but are not limited to, blood, whole blood, plasma, serum, urine, cerebrospinal fluid, fecal, saliva, sweat, tears, pleural fluid, pericardial fluid, or peritoneal fluid of the subject. In some embodiments, the biological sample consists of blood, whole blood, plasma, serum, urine, cerebrospinal fluid, fecal, saliva, sweat, tears, pleural fluid, pericardial fluid, or peritoneal fluid of the subject. In such embodiments, the biological sample is limited to blood, whole blood, plasma, serum, urine, cerebrospinal fluid, fecal, saliva, sweat, tears, pleural fluid, pericardial fluid, or peritoneal fluid of the subject and does not contain other components (e.g., solid tissues, etc.) of the subject. A biological sample can include any tissue or material derived from a living or dead subject. A biological sample can be a cell-free sample. A biological sample can comprise a nucleic acid (e.g., DNA or RNA) or a fragment thereof. The term "nucleic acid" can refer to deoxyribonucleic acid (DNA), ribonucleic acid (RNA) or any hybrid or fragment thereof. The nucleic acid in the sample can be a cell-free nucleic acid. A sample can be a liquid sample or a solid sample (e.g., a cell or tissue sample). A biological sample can be a bodily fluid, such as blood, plasma, serum, urine, vaginal fluid, fluid from a hydrocele (e.g., of the testis), vaginal flushing fluids, pleural fluid, ascitic fluid, cerebrospinal fluid, saliva, sweat, tears, sputum, bronchoalveolar lavage fluid, discharge fluid from the nipple, aspiration fluid from different parts of the body (e.g., thyroid, breast), etc. A biological sample can be a stool sample. In various embodiments, the majority of DNA in a biological sample that has been enriched for cell-free DNA (e.g., a plasma sample obtained via a centrifugation protocol) can be cell-free (e.g., greater than 50%, 60%, 70%, 80%, 90%, 95%, or 99% of the DNA can be cell-free). A biological sample can be treated to physically disrupt tissue or cell structure (e.g., centrifugation and/or cell lysis), thus releasing intracellular components into a solution which can further contain enzymes, buffers, salts, detergents, and the like which can be used to prepare the sample for analysis. A biological sample can be obtained from a subject invasively (e.g., surgical means) or non-invasively (e.g., a blood draw, a swab, or collection of a discharged sample).

As used herein, the terms "nucleic acid" and "nucleic acid molecule" are used interchangeably. The terms refer to nucleic acids of any composition form, such as deoxyribonucleic acid (DNA, e.g., complementary DNA (cDNA), genomic DNA (gDNA) and the like), and/or DNA analogs (e.g., containing base analogs, sugar analogs and/or a non-native backbone and the like), all of which can be in single- or double-stranded form. Unless otherwise limited, a nucleic acid can comprise known analogs of natural nucleotides, some of which can function in a similar manner as naturally occurring nucleotides. A nucleic acid can be in any form useful for conducting processes herein (e.g., linear, circular, supercoiled, single-stranded, double-stranded and the like). A nucleic acid in some embodiments can be from a single chromosome or fragment thereof (e.g., a nucleic acid sample may be from one chromosome of a sample obtained from a diploid organism). In certain embodiments nucleic acids comprise nucleosomes, fragments or parts of nucleosomes or nucleosome-like structures. Nucleic acids sometimes comprise protein (e.g., histones, DNA binding proteins, and the like). Nucleic acids analyzed by processes described herein sometimes are substantially isolated and are not substantially associated with protein or other molecules. Nucleic acids also include derivatives, variants and analogs of DNA synthesized, replicated or amplified from single-stranded ("sense" or "antisense," "plus" strand or "minus" strand, "forward" reading frame or "reverse" reading frame) and double-stranded polynucleotides. Deoxyribonucleotides include deoxyadenosine, deoxycytidine, deoxyguanosine and deoxythymidine. A nucleic acid may be prepared using a nucleic acid obtained from a subject as a template.

As used herein, the term "cell-free nucleic acids" refers to nucleic acid molecules that can be found outside cells, in bodily fluids such as blood, whole blood, plasma, serum, urine, cerebrospinal fluid, fecal, saliva, sweat, sweat, tears, pleural fluid, pericardial fluid, or peritoneal fluid of a subject. Cell-free nucleic acids originate from one or more healthy cells and/or from one or more cancer cells Cell-free nucleic acids are used interchangeably as circulating nucleic acids. Examples of the cell-free nucleic acids include but are not limited to RNA, mitochondrial DNA, or genomic DNA. As used herein, the terms "cell free nucleic acid," "cell free DNA," and "cfDNA" are used interchangeably. As used herein, the term "circulating tumor DNA" or "ctDNA" refers to nucleic acid fragments that originate from tumor cells or other types of cancer cells, which may be released into a fluid from an individual's body (e.g., bloodstream) as result of biological processes such as apoptosis or necrosis of dying cells or actively released by viable tumor cells.

It will be understood that, due to specific binding and subsequent enrichment of target molecules on the sample reaction nanostructures, it is possible to utilize devices and methods disclosed herein to detect any marker or molecule (e.g., protein or nucleic acid) representative of a disease condition. In some embodiments, the device and method can be used to determine a stage of any applicable cancer condition. In some embodiments, the device and method can be used to detect a disease condition of an unborn fetus or the pregnant mother.

The device includes a plurality of components including, but not limited to, a needle or cannula having a body comprising an addressable, patterned plurality of sample reaction nanostructures.

In some embodiments, the body of the device has a length between about 10 mm to about 200 mm, e.g., about 10 mm, about 15 mm, about 20 mm, about 25 mm, about 30 mm, about 35 mm, about 40 mm, about 45 mm, about 50 mm, about 55 mm, about 60 mm, about 65 mm, about 70 mm, about 75 mm about 80 mm, about 85 mm, about 90 mm, about 95 mm, about 100 mm, about 110 mm, about 115 mm, about 120 mm, about 125 mm, about 130 mm, about 135 mm, about 140 mm, about 145 mm, about 150 mm, about 155 mm, about 160 mm, about 165 mm, about 170 mm, about 175 mmm about 180 mm, about 185 mm, about 190 mm, about 195 mm, about 200 mm, about 10 mm to about 200 mm, about 10 mm to about 150 mm, about 10 mm to about 100 mm, about 15 mm to about 200 mm, about 20 mm to about 200 mm, about 30 mm to about 200 mm, about 35 mm to about 200 mm, about 40 mm to about 200 mm, about 50 mm to about 200 mm, about 60 mm to about 200 mm, about 70 mm to about 200 mm, about 80 mm to about 200 mm, about 90 mm to about 200 mm, about 100 mm to about 200 mm, about 110 mm to about 200 mm, about 120 mm to about 200 mm, about 130 mm to about 200 mm, about 140 mm to about 200 mm, about 150 mm to about 200 mm, about 160 mm to about 200 mm, about 170 mm to about 200 mm, about 180 mm to about 200 mm, about 190 mm to about 200 mm, about 50 mm to about 150 mm, about 50 mm to about 180 mm, about 80 mm to about 190 mm, about 80 mm to about 180 mm, about 70 mm to about 170 mm, or about 60 mm to about 160 mm.

In some embodiments, the average inner diameter of the body of the needle is at least about 1 µm, e.g., about 1 µm, about 2 µm, about 5 µm, about 10 µm, about 15 µm, about 20 µm, about 25 µm, about 30 µm, about 35 µm, about 40 µm, about 45 µm, about 50 µm, about 55 µm, about 60 µm, about 65 µm, about 70 µm, about 75 µm, about 80 µm, about 85 µm, about 90 µm, about 95 µm, about 100 µm, about 105 µm, about 110 µm, about 115 µm, about 120 µm, about 125 µm, about 130 µm, about 135 µm, about 140 µm, about 145 µm, about 150 µm, about 155 µm, about 160 µm, about 165 µm, about 170 µm, about 175 µm, about 180 µm, about 185 µm, about 190 µm, about 195 µm, about 200 µm, about 205 µm, about 210 µm, about 215 µm, about 220 µm, about 225 µm, about 230 µm, about 235 µm, about 240 µm, about 245 µm, about 250 µm, about 255 µm, about 260 µm, about 265 µm, about 270 µm, about 275 µm, about 280 µm, about 285 µm, about 290 µm, about 295 µm, about 300 µm, or more. In some embodiments, the needle can be of a sufficient size to be injected into a blood vessel of a human subject.

In some embodiments, the needle body is made of steel, e.g., stainless steel. In some embodiments, the surface, e.g., inner surface and/or outer surface of the needle body is coated with a coating layer or a deposit layer. In other embodiments, the inner and/or outer surfaces of the needle body include a deposit layer. In some cases, the deposit layer has an average thickness of up to about 40 Ångströms (Å), e.g., about 1 Å, about 2 Å, about 3 Å, about 4 Å, about 5 Å, about 6 Å, about 7 Å, about 8 Å, about 9 Å, about 10 Å, about 11 Å, about 12 Å, about 13 Å, about 14 Å, about 15 Å, about 16 Å, about 17 Å, about 18 Å, about 19 Å, about 20 Å, about 21 Å, about 22 Å, about 23 Å, about 24 Å, about 25 Å, about 26 Å, about 27 Å, about 28 Å, about 29 Å, about 30 Å, about 31 Å, about 32 Å, about 33 Å, about 34 Å, about 35 Å, about 36 Å, about 37 Å, about 38 Å, about 39 Å, or about 40 Å. In other cases, the deposit layer has an average thickness of up to about 20 Ångströms (Å), e.g., about 1 Å, about 2 Å, about 3 Å, about 4 Å, about 5 Å, about 6 Å, about 7 Å, about 8 Å, about 9 Å, about 10 Å, about 11 Å, about 12 Å, about 13 Å, about 14 Å, about 15 Å, about 16 Å, about 17 Å, about 18 Å, about 19 Å, or about 20 Å.

In some embodiments, the deposit layer comprises a non-corrosive metal, a non-corrosive alloy, nanoparticles, an element, a polymer, gold, platinum, an alloy, carbon, titanium dioxide, aluminum oxide, or a combination thereof.

In some embodiments, the needle body is injected or inserted into any blood vessel of the subject. In some embodiments, the needle body is injected into a solid tumor or near a solid tumor in the subject. In some embodiments, the target molecule contacts the inner surface of the body of the needle. In other embodiments, the target molecule contacts the outer surface of the body.

In some embodiments, the device is inserted into the bloodstream via a blood vessel of a subject for about at least 1 minute. In some embodiments, the needle remains in the blood vessel for about 1 minute to about 15 minutes, e.g., about 1-15 minutes, about 2-15 minutes, about 3-15 minutes, about 4-15 minutes, about 5-15 minutes, about 6-15 minutes, about 7-15 minutes, about 8-15 minutes, about 9-15 minutes, about 10-15 minutes, about 1-10 minutes, about 5-10 minutes, about 7-15 minutes, about 8-15 minutes, about 11-15 minutes, or about 12-15 minutes. In some embodiments, the needle remains in the blood vessel for about 5-20 minutes, about 10-20 minutes, about 5-15 minutes, about 15-20 minutes, or more. In certain embodiments, the device is inserted into the bloodstream via a blood vessel of a subject for less than 1 minute.

The body of the device may comprise a substrate onto which a number of sample reaction nanostructures may be disposed. Within each nanostructure, reagents of the diagnostic system described herein are applied to the nanostructures. Each nanostructure may contain the same or similar reagents except for a different target binding molecule, such as but not limited to a different guide RNA or a different antigen binding molecule. Optionally, each nanostructure may contain the same or similar reagents except for different sets of target binding molecules. In some embodiments, the needle comprises 100 to 1000 sample reaction nanostructures, e.g., about 100-1000 sample reaction nanostructures, about 100-500 sample reaction nanostructures, about 100-800 sample reaction nanostructures, about 500-1000 sample reaction nanostructures, about 700-1000 sample reaction nanostructures, about 100 sample reaction nanostructures, about 200 sample reaction nanostructures, about 300 sample reaction nanostructures, about 400 sample reaction nanostructures, about 500 sample reaction nanostructures, about 600 sample reaction nanostructures, about 700 sample reaction nanostructures, about 800 sample reaction nanostructures, about 900 sample reaction nanostructures, or about 1000 sample reaction nanostructures.

In some embodiments, the sample reaction nanostructures are on the outer surface of the body of the needle. In some cases, the biological sample contacts the sample reaction nanostructures located on the outer surface of the needle body.

In some embodiments, the sample reaction nanostructures are on the inner surface of the body of the needle. In certain embodiments, the sample reaction nanostructures are located on the luminal surface (e.g., inside surface) of the needle. For instance, the biological sample flows through an opening into the inside of the needle to the sample reaction nanostructures. In some embodiments, the biological sample enters to needle through an opening and flows along the center bore of the body of the needle.

In some embodiments, the needle body comprises one or more openings (e.g., holes or pores). In some embodiments, the needle body comprises an opening at one end of the needle to allow the biological sample to enter the lumen or center bore of the needle. In certain embodiments, the needle body has a plurality of openings on the length of the needle body. In some instances, the openings of the plurality are on a portion of the body. In certain instances, the openings are on the entire body. In some embodiments, the openings of the plurality are radially spaced apart. In particular embodiments, the openings are equally spaced apart.

In some embodiments, the body of the needle comprises no openings for the biological sample to enter the lumen or center bore of the needle. In one embodiment, the needle body resembles a probe comprising sample reaction nanostructures on its outer surface.

In some embodiments, the device or components of the device are for single use. The diagnostic device or any one of the components of the device can be disposable after a single use. In some cases, at least one component of the device is placed on a single use substrate.

The devices may further comprise inlet and outlet ports, syringes, openings which may be connect to valves, tubes, channels and/or pumps. In some cases, the devices are connected to controllers with programmable valves to move fluids and/or the sample through the device.

In some embodiments, the sample reaction nanostructures on the surface of the needle body are arranged to form an organized and arrayed pattern. Each sample reaction nanostructure can be located at a spatially addressable position on the surface of the needle body. Such sample reaction nanostructures can be disposed on the needle body by lithography (e.g., laser lithography), laser scribing, vapor deposition followed by etching or scribing, 3-D printing, or any other applicable methods of microfabrication.

In some embodiments, the sample reaction nanostructure includes reagents useful for the CRISPR-based assay described herein. In other embodiments, the sample reaction nanostructure includes reagents useful for the CTC-based assay described herein. The reagents of the assays described below may be freeze-dried or lyophilized.

III. CRISPR-Based Devices and Assays

The CRISPR-based assays described herein utilize DNA endonucleases (e.g., Cas12/Cas13/Csm6 proteins) that cleave a target nucleic acid sequence, as well as non-target nucleic acids (e.g., non-target DNA and non-target RNA) when the DNA endonucleases remain active. Cas12/Cas13/Csm6 proteins are programmed to detect specific target nucleic acid sequences through synthesis of and incubation with specific RNA guide molecules. The RNA guide molecules specific to different cancer markers can be printed onto the needle tip of a diagnostic device in a patterned manner, such that it is possible to correlate the location on the needle to the target nucleic acid sequence that is recognized. The needle tip can be inserted into the blood for at least 1 minute in order to allow the full volume of the patient's blood to contact the tip. If the Cas12/Cas13/Csm6 protein is activated upon recognizing its target nucleic acid, it will also cleave non-target nucleic acid reporter molecules that can be detected. Each addressable assay can be monitored by detecting the presence of the reporter molecules, thus forming a patient-specific cancer profile that can be used to diagnose cancer or monitor cancer progression.

A. Circulating Cell-Free Nucleic Acids

Circulating cell-free nucleic acids can include potentially useful biomarkers for various cancer conditions including, but not limited to, early stage cancer conditions. Specific cancer markers that indicate cancer can be detected in the cell-free nucleic acids (e.g., cfDNA and cfRNA). The present invention utilizes a CRISPR-based assay to detect mutations in cancer markers such as, but not limited to, TP53, PIK3CA, PTEN, APC, VHL, KRAS, MLL3, MLL2, ARID1A, PBRM1, NAV3, EGFR, NF1, PIK3R1, CDKN2A, GATA3, RB1, NOTCH1, FBXW7, CTNNB1, DNMT3A, MAP3K1, FLT3, MALAT1, TSHZ3, KEAP1, CDH1, ARHGAP35, CTCF, NFE2L2, SETBP1, BAP1, NPM1, RUNX1, NRAS, IDH1, TBX3, MAP2K4, RPL22, STK11, CRIPAK, CEBPA, KDM6A, EPHA3, AKT1, STAG2, BRAF, AR, AJUBA, EPPK1, TSHZ2, PIK3CG, SOX9, ATM, CDKN1B, WT1, HGF, KDM5C, PRX, ERBB4, MTOR, TLR4, U2AF1, ARID5B, TET2, ATRX, MLL4, ELF3, BRCA1, LRRK2, POLQ, FOXA1, IDH2, CHEK2, KIT, HIST1H1C, SETD2, PDGFRA, EP300, FGFR2, CCND1, EPHB6, SMAD4, FOXA2, USP9X, BRCA2, NFE2L3, FGFR3, ASXL1, TGFBR2, SOX17, CDKN1A, B4GALT3, SF3B1, TAF1, PPP2R1A, CBFB, ATR, SIN3A, VEZF1, HIST1H2BD, EIF4A2, CDK12, PHF6, SMC1A, PTPN11, ACVR1B, MAPK8IP1, H3F3C, NSD1, TBL1XR1, EGR3, ACVR2A, MECOM, LIFR, SMC3, NCOR1, RPL5, SMAD2, SPOP, AXIN2, MIR142, RAD21, ERCC2, CDKN2C, EZH2, and PCBP1.

As used herein, the term "mutation," refers to a detectable change in the genetic material of one or more cells. In a particular example, one or more mutations can be found in, and can identify, cancer cells (e.g., driver and passenger mutations). A mutation can be transmitted from apparent cell to a daughter cell. A person having skill in the art will appreciate that a genetic mutation (e.g., a driver mutation) in a parent cell can induce additional, different mutations (e.g., passenger mutations) in a daughter cell. A mutation generally occurs in a nucleic acid. In a particular example, a mutation can be a detectable change in one or more deoxyribonucleic acids or fragments thereof. A mutation generally refers to nucleotides that is added, deleted, substituted for, inverted, or transposed to a new position in a nucleic acid. A mutation can be a spontaneous mutation or an experimentally induced mutation. A mutation in the sequence of a particular tissue is an example of a "tissue-specific allele." For example, a tumor can have a mutation that results in an allele at a locus that does not occur in normal cells. Another example of a "tissue-specific allele" is a fetal-specific allele that occurs in the fetal tissue, but not the maternal tissue.

In some embodiments, the presence of one or more mutations (e.g., a variation, substitution, deletion, or addition to the nucleic acid sequence) are detected in one or more target sequences selected from the group consisting of TP53, PIK3CA, PTEN, APC, VHL, KRAS, MLL3, MLL2, ARID1A, PBRM1, NAV3, EGFR, NF1, PIK3R1, CDKN2A, GATA3, RB1, NOTCH1, FBXW7, CTNNB1, DNMT3A, MAP3K1, FLT3, MALAT1, TSHZ3, KEAP1, CDH1, ARHGAP35, CTCF, NFE2L2, SETBP1, BAP1, NPM1, RUNX1, NRAS, IDH1, TBX3, MAP2K4, RPL22, STK11, CRIPAK, CEBPA, KDM6A, EPHA3, AKT1, STAG2, BRAF, AR, AJUBA, EPPK1, TSHZ2, PIK3CG, SOX9, ATM, CDKN1B, WT1, HGF, KDM5C, PRX, ERBB4, MTOR, TLR4, U2AF1, ARID5B, TET2, ATRX, MLL4, ELF3, BRCA1, LRRK2, POLQ, FOXA1, IDH2, CHEK2, KIT, HIST1H1C, SETD2, PDGFRA, EP300, FGFR2, CCND1, EPHB6, SMAD4, FOXA2, USP9X, BRCA2, NFE2L3, FGFR3, ASXL1, TGFBR2, SOX17, CDKN1A, B4GALT3, SF3B1, TAF1, PPP2R1A, CBFB, ATR, SIN3A, VEZF1, HIST1H2BD, EIF4A2, CDK12, PHF6, SMC1A, PTPN11, ACVR1B, MAPK8IP1, H3F3C, NSD1, TBL1XR1, EGR3, ACVR2A, MECOM, LIFR, SMC3, NCOR1, RPL5, SMAD2, SPOP, AXIN2, MIR142, RAD21, ERCC2, CDKN2C, EZH2, and PCBP1.

In some cases, one or more mutations are detected in a single target sequence selected from the group consisting of TP53, PIK3CA, PTEN, APC, VHL, KRAS, MLL3, MLL2, ARID1A, PBRM1, NAV3, EGFR, NF1, PIK3R1, CDKN2A, GATA3, RB1, NOTCH1, FBXW7, CTNNB1, DNMT3A, MAP3K1, FLT3, MALAT1, TSHZ3, KEAP1, CDH1, ARHGAP35, CTCF, NFE2L2, SETBP1, BAP1, NPM1, RUNX1, NRAS, IDH1, TBX3, MAP2K4, RPL22, STK11, CRIPAK, CEBPA, KDM6A, EPHA3, AKT1, STAG2, BRAF, AR, AJUBA, EPPK1, TSHZ2, PIK3CG, SOX9, ATM, CDKN1B, WT1, HGF, KDM5C, PRX, ERBB4, MTOR, TLR4, U2AF1, ARID5B, TET2, ATRX, MLL4, ELF3, BRCA1, LRRK2, POLQ, FOXA1, IDH2, CHEK2, KIT, HIST1H1C, SETD2, PDGFRA, EP300, FGFR2, CCND1, EPHB6, SMAD4, FOXA2, USP9X, BRCA2, NFE2L3, FGFR3, ASXL1, TGFBR2, SOX17, CDKN1A, B4GALT3, SF3B1, TAF1, PPP2R1A, CBFB, ATR, SIN3A, VEZF1, HIST1H2BD, EIF4A2, CDK12, PHF6, SMC1A, PTPN11, ACVR1B, MAPK8IP1, H3F3C, NSD1, TBL1XR1, EGR3, ACVR2A, MECOM, LIFR, SMC3, NCOR1, RPL5, SMAD2, SPOP, AXIN2, MIR142, RAD21, ERCC2, CDKN2C, EZH2, and PCBP1.

In some embodiments, the presence of a mutation(s) is detected in at least two target sequences selected from the group consisting of TP53, PIK3CA, PTEN, APC, VHL, KRAS, MLL3, MLL2, ARID1A, PBRM1, NAV3, EGFR, NF1, PIK3R1, CDKN2A, GATA3, RB1, NOTCH1, FBXW7, CTNNB1, DNMT3A, MAP3K1, FLT3, MALAT1, TSHZ3, KEAP1, CDH1, ARHGAP35, CTCF, NFE2L2, SETBP1, BAP1, NPM1, RUNX1, NRAS, IDH1, TBX3, MAP2K4, RPL22, STK11, CRIPAK, CEBPA, KDM6A, EPHA3, AKT1, STAG2, BRAF, AR, AJUBA, EPPK1, TSHZ2, PIK3CG, SOX9, ATM, CDKN1B, WT1, HGF, KDM5C, PRX, ERBB4, MTOR, TLR4, U2AF1, ARID5B, TET2, ATRX, MLL4, ELF3, BRCA1, LRRK2, POLQ, FOXA1, IDH2, CHEK2, KIT, HIST1H1C, SETD2, PDGFRA, EP300, FGFR2, CCND1, EPHB6, SMAD4, FOXA2, USP9X, BRCA2, NFE2L3, FGFR3, ASXL1, TGFBR2, SOX17, CDKN1A, B4GALT3, SF3B1, TAF1, PPP2R1A, CBFB, ATR, SIN3A, VEZF1, HIST1H2BD, EIF4A2, CDK12, PHF6, SMC1A, PTPN11, ACVR1B, MAPK8IP1, H3F3C, NSD1, TBL1XR1, EGR3, ACVR2A, MECOM, LIFR, SMC3, NCOR1, RPL5, SMAD2, SPOP, AXIN2, MIR142, RAD21, ERCC2, CDKN2C, EZH2, and PCBP1. In one embodiment, 1, 2, 3, 4, 5, or more mutations are detected in a first target sequence and 1, 2, 3, 4, 5, or more mutations are detected in a second target sequence, wherein the first and second target sequences are selected from the group consisting of TP53, PIK3CA, PTEN, APC, VHL, KRAS, MLL3, MLL2, ARID1A, PBRM1, NAV3, EGFR, NF1, PIK3R1, CDKN2A, GATA3, RB1, NOTCH1, FBXW7, CTNNB1, DNMT3A, MAP3K1, FLT3, MALAT1, TSHZ3, KEAP1, CDH1, ARHGAP35, CTCF, NFE2L2, SETBP1, BAP1, NPM1, RUNX1, NRAS, IDH1, TBX3, MAP2K4, RPL22, STK11, CRIPAK, CEBPA, KDM6A, EPHA3, AKT1, STAG2, BRAF, AR, AJUBA, EPPK1, TSHZ2, PIK3CG, SOX9, ATM, CDKN1B, WT1, HGF, KDM5C, PRX, ERBB4, MTOR, TLR4, U2AF1, ARID5B, TET2, ATRX, MLL4, ELF3, BRCA1, LRRK2, POLQ, FOXA1, IDH2, CHEK2, KIT, HIST1H1C, SETD2, PDGFRA, EP300, FGFR2, CCND1, EPHB6, SMAD4, FOXA2, USP9X, BRCA2, NFE2L3, FGFR3, ASXL1, TGFBR2, SOX17, CDKN1A, B4GALT3, SF3B1, TAF1, PPP2R1A, CBFB, ATR, SIN3A, VEZF1, HIST1H2BD, EIF4A2, CDK12, PHF6, SMC1A, PTPN11, ACVR1B, MAPK8IP1, H3F3C, NSD1, TBL1XR1, EGR3, ACVR2A, MECOM, LIFR, SMC3, NCOR1, RPL5, SMAD2, SPOP, AXIN2, MIR142, RAD21, ERCC2, CDKN2C, EZH2, and PCBP1, and the first and second target sequences are unique. In another embodiment, 1, 2, 3, 4, 5, or more mutations are detected in a first target sequence; 1, 2, 3, 4, 5, or more mutations are detected in a second target sequence; and 1, 2, 3, 4, 5, or more mutations are detected in a third target sequence, wherein the first, second and third target sequences are selected from the group consisting of TP53, PIK3CA, PTEN, APC, VHL, KRAS, MLL3, MLL2, ARID1A, PBRM1, NAV3, EGFR, NF1, PIK3R1, CDKN2A, GATA3, RB1, NOTCH1, FBXW7, CTNNB1, DNMT3A, MAP3K1, FLT3, MALAT1, TSHZ3, KEAP1, CDH1, ARHGAP35, CTCF, NFE2L2, SETBP1, BAP1, NPM1, RUNX1, NRAS, IDH1, TBX3, MAP2K4, RPL22, STK11, CRIPAK, CEBPA, KDM6A, EPHA3, AKT1, STAG2, BRAF, AR, AJUBA, EPPK1, TSHZ2, PIK3CG, SOX9, ATM, CDKN1B, WT1, HGF, KDM5C, PRX, ERBB4, MTOR, TLR4, U2AF1, ARID5B, TET2, ATRX, MLL4, ELF3, BRCA1, LRRK2, POLQ, FOXA1, IDH2, CHEK2, KIT, HIST1H1C, SETD2, PDGFRA, EP300, FGFR2, CCND1, EPHB6, SMAD4, FOXA2, USP9X, BRCA2, NFE2L3, FGFR3, ASXL1, TGFBR2, SOX17, CDKN1A, B4GALT3, SF3B1, TAF1, PPP2R1A, CBFB, ATR, SIN3A, VEZF1, HIST1H2BD, EIF4A2, CDK12, PHF6, SMC1A, PTPN11, ACVR1B, MAPK8IP1, H3F3C, NSD1, TBL1XR1, EGR3, ACVR2A, MECOM, LIFR, SMC3, NCOR1, RPL5, SMAD2, SPOP, AXIN2, MIR142, RAD21, ERCC2, CDKN2C, EZH2, and PCBP1, and the first, second, and third target sequences are unique. In some embodiments, the presence of a mutation(s) (e.g., at least one or more mutations) is detected in at least 2 to at least 100 target sequences in the group provided herein. In some embodiments, the presence of a mutation(s) is detected in at least 2 to at least 120 target sequences in the group provided herein. In some embodiments, the presence of a mutation(s) is detected in at least 10 to at least 110 target sequences in the group provided herein. In some embodiments, the presence of a mutation(s) is detected in at least 20 to at least 120 target sequences in the group provided herein.

In some cases, mutations are detected in about 2, 5, 10, 15, 20, 25, 30, 35, 40, 45, 50, 55, 60, 65, 70, 75, 80, 85, 90, 95, 100, 105, 110, 115, 120, 125, or more target sequences selected from the group consisting of TP53, PIK3CA, PTEN, APC, VHL, KRAS, MLL3, MLL2, ARID1A, PBRM1, NAV3, EGFR, NF1, PIK3R1, CDKN2A, GATA3, RB1, NOTCH1, FBXW7, CTNNB1, DNMT3A, MAP3K1, FLT3, MALAT1, TSHZ3, KEAP1, CDH1, ARHGAP35, CTCF, NFE2L2, SETBP1, BAP1, NPM1, RUNX1, NRAS, IDH1, TBX3, MAP2K4, RPL22, STK11, CRIPAK, CEBPA, KDM6A, EPHA3, AKT1, STAG2, BRAF, AR, AJUBA, EPPK1, TSHZ2, PIK3CG, SOX9, ATM, CDKN1B, WT1, HGF, KDM5C, PRX, ERBB4, MTOR, TLR4, U2AF1, ARID5B, TET2, ATRX, MLL4, ELF3, BRCA1, LRRK2, POLQ, FOXA1, IDH2, CHEK2, KIT, HIST1H1C, SETD2, PDGFRA, EP300, FGFR2, CCND1, EPHB6, SMAD4, FOXA2, USP9X, BRCA2, NFE2L3, FGFR3, ASXL1, TGFBR2, SOX17, CDKN1A, B4GALT3, SF3B1, TAF1, PPP2R1A, CBFB, ATR, SIN3A, VEZF1, HIST1H2BD, EIF4A2, CDK12, PHF6, SMC1A, PTPN11, ACVR1B, MAPK8IP1, H3F3C, NSD1, TBL1XR1, EGR3, ACVR2A, MECOM, LIFR, SMC3, NCOR1, RPL5, SMAD2, SPOP, AXIN2, MIR142, RAD21, ERCC2, CDKN2C, EZH2, and PCBP1.

In some embodiments, the presence of a mutation(s) (e.g., a variation, substitution, deletion, or addition to the nucleic acid sequence) is detected in one or more target sequences selected from the group consisting of P53, PIK3CA, MAP3KI, MAP2K4, PIK3R1, LPA, KRAS, ERBB2, FGFR2, and TNXB. In some cases, one or more mutations (e.g., 1, 2, 3, 4, 5, 6, 7, 8, 9, 10 or more mutations) are detected in a single target sequence selected from P53, PIK3CA, MAP3KI, MAP2K4, PIK3R1, LPA, KRAS, ERBB2, FGFR2, or TNXB. In some embodiments, one or more mutations are detected in P53. In some embodiments, one or more mutations are detected in PIK3CA. In some embodiments, one or more mutations are detected in MAP3KI. In some embodiments, one or more mutations are detected in MAP2K4. In some embodiments, one or more mutations are detected in PIK3R1. In some embodiments, one or more mutations are detected in LPA. In some embodiments, one or more mutations are detected in KRAS. In some embodiments, one or more mutations are detected in ERBB2. In some embodiments, one or more mutations are detected in FGFR2. In some embodiments, one or more mutations are detected in TNXB. In some embodiments, the presence of a mutation(s) is detected in at least two target sequences selected from the group consisting of P53, PIK3CA, MAP3KI, MAP2K4, PIK3R1, LPA, KRAS, ERBB2, FGFR2, and TNXB. In some embodiments, mutations are detected in P53 and at least one other target sequence selected from the group consisting of PIK3CA, MAP3KI, MAP2K4, PIK3R1, LPA, KRAS, ERBB2, FGFR2, and TNXB. In some embodiments, mutations are detected in PIK3CA and at least one other target sequence selected from the group consisting of P53, MAP3KI, MAP2K4, PIK3R1, LPA, KRAS, ERBB2, FGFR2, and TNXB. In some embodiments, mutations are detected in MAP3KI and at least one other target sequence selected from the group consisting of PIK3CA, MAP2K4, PIK3R1, LPA, KRAS, ERBB2, FGFR2, and TNXB. In some embodiments, mutations are detected in MAP2K4 and at least one other target sequence selected from the group consisting of P53, PIK3CA, MAP3KI, PIK3R1, LPA, KRAS, ERBB2, FGFR2, and TNXB. In some embodiments, mutations are detected in PIK3R1 and at least one other target sequence selected from the group consisting of P53, PIK3CA, MAP3KI, MAP2K4, LPA, KRAS, ERBB2, FGFR2, and TNXB. In some embodiments, mutations are detected in LPA and at least one other target sequence selected from the group consisting of PIK3CA, MAP3KI, MAP2K4, PIK3R1, KRAS, ERBB2, FGFR2, and TNXB. In some embodiments, mutations are detected in KRAS and at least one other target sequence selected from the group consisting of P53, PIK3CA, MAP3KI, MAP2K4, PIK3R1, LPA, ERBB2, FGFR2, and TNXB. In some embodiments, mutations are detected in ERBB2 and at least one other target sequence selected from the group consisting of P53, PIK3CA, MAP3KI, MAP2K4, PIK3R1, LPA, KRAS, FGFR2, and TNXB. In some embodiments, mutations are detected in FGFR2 and at least one other target sequence selected from the group consisting of PIK3CA, MAP3KI, MAP2K4, PIK3R1, LPA, KRAS, ERBB2, and TNXB. In some embodiments, mutations are detected in TNXB and at least one other target sequence selected from the group consisting of P53, PIK3CA, MAP3KI, MAP2K4, PIK3R1, LPA, KRAS, ERBB2, and FGFR2. In some cases, mutations are detected in 2, 3, 4, 5, 6, 7, 8, 9, or 10 target sequences selected from the group consisting of P53, PIK3CA, MAP3KI, MAP2K4, PIK3R1, LPA, KRAS, ERBB2, FGFR2, and TNXB. In certain instances, a mutation(s) in P53 and in one or more other target sequences are detected. In some instances, a mutation(s) in PIK3CA and in one or more other target sequences are detected. In other instances, a mutation(s) in MAP3KI and in one or more other target sequences are detected. In particular instances, a mutation(s) in MAP2K4 and in one or more other target sequences are detected. In certain instances, a mutation(s) in PIK3R1 and in one or more other target sequences are detected. In some instances, a mutation(s) in LPA and in one or more other target sequences are detected. In particular instances, a mutation(s) in KRAS and in one or more other target sequences are detected. In some instances, a mutation(s) in ERBB2 and in one or more other target sequences are detected. In certain instances, a mutation(s) in FGFR2 and in one or more other target sequences are detected. In some instances, a mutation(s) in TNXB and in one or more other target sequences are detected.

In some embodiments, the presence of a mutation(s) (e.g., a variation, substitution, deletion, or addition to the nucleic acid sequence) is detected in one or more target sequences selected from the group consisting of AKT1, BRAF, EGFR, KRAS, MAP2K1, NRAS, PI3KCA, and PTEN. In some cases, one or more mutations (e.g., 1, 2, 3, 4, 5, 6, 7, 8, 9, 10 or more mutations) are detected in a single target sequence selected from AKT1, BRAF, EGFR, KRAS, MAP2K1, NRAS, PI3KCA, and PTEN. In some cases, mutations are detected in 2, 3, 4, 5, 6, 7, 8, 9, or 10 target sequences selected from the group consisting of AKT1, BRAF, EGFR, KRAS, MAP2K1, NRAS, PI3KCA, and PTEN. In some embodiments, the mutations comprise one or more selected from the group consisting of AKT1-E17K, BRAF-V600E, BRAF-L597V, BRAF-G469A, BRAF-G466V, EGFR-E709 T710delins, EGFR-G719S, EGFR-G719C, EGFR-G719A, EGFR-Exonl9del, EGFR-T790M, EGFR-L858R, EGFR-L861Q, KRAS-Q61H, KRAS-Q61L, KRAS-Q61R, KRAS-Q61K, KRAS-G13A, KRAS-G13D, KRAS-G13C, KRAS-G13R, KRAS-G13D, KRAS-G13C, KRAS-G13R, KRAS-G13S, KRAS-G12V, KRAS-G12A, KRAS-G12D, KRAS-G12D, KRAS-G12C, KRAS-G12R, KRAS-G12S, MAP2K1-Q56P, NRAS-Q61H, NRAS-Q61L, NRAS-Q61R, NRAS-Q61K, NRAS-G12A, NRAS-G12D, NRAS-G12C, NRAS-G12R, NRAS-G12S, PI3KCA-E542K, PI3KCA-E545Q, PI3KCA-E545K, PI3KCA-H1047R, PI3KCA-H1047L, and PTEN-R233* mutations.

In a CRISPR complex, "target sequence" refers to a nucleic acid sequence to which a guide sequence is designed to have complementarity, where hybridization between a target sequence and a guide sequence promotes the formation of a CRISPR-Cas complex. A target sequence may comprise RNA polynucleotides. The term "target RNA" refers to an RNA polynucleotide being or comprising the target sequence. In other words, the target RNA may be an RNA polynucleotide or a part of an RNA polynucleotide to which a part of the gRNA, i.e. the guide sequence or crRNA, is designed to have complementarity and to which the effector function mediated by the complex comprising a Cas protein and a gRNA (e.g., crRNA) is to be directed. In some embodiments, cell-free RNA located in the circulating blood of a subject, e.g., human subject comprises the target RNA.

In some embodiments, a target sequence comprises DNA polynucleotides. The term "target DNA" refers to a DNA polynucleotide being or comprising the target sequence. In some embodiments, cell-free DNA located in the circulating blood of a subject, e.g., human subject comprises the target DNA.

B. Cas Proteins

In some embodiments, the Cas protein of the assay includes, but is not limited to, Cas1, Cas1B, Cas2, Cas3, Cas4, Cas5, Cash, Cas7, Cas8, Cas9 (also known as Csn1 and Csx12), Cas12a, Cas13, Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologues thereof, orthologues thereof, or modified versions thereof. In some embodiments, the Cas protein comprises one or more mutations. Such mutations can be in a catalytic domain.

In some embodiments, a homologue or orthologue of a Cas protein, for instance, a Cas13 protein, has a sequence identity of at least 30%, or at least 40%, or at least 50%, or at least 60%, or at least 70%, or at least 80%, more preferably at least 85%, even more preferably at least 90%, such as for instance at least 95% to a Cas13 protein based on the wild-type sequence of any of *Leptotrichia shahii* Cas13, *Lachnospiraceae bacterium* MA2020 Cas13, *Lachnospiraceae bacterium* NK4A179 C2c2, *Clostridium aminophilum* (DSM 10710) Cas13, *Carnobacterium gallinarum* (DSM 4847) Cas13, *Paludibacter propionicigenes* (WB4) C2c2, *Listeria weihenstephanensis* (FSL R9-0317) Cas13, *Listeriaceae bacterium* (FSL M6-0635) Cas13, *Listeria newyorkensis* (FSL M6-0635) Cas13, *Leptotrichia wadei* (F0279) Cas13, *Rhodobacter capsulatus* (SB 1003) Cas13, *Rhodobacter capsulatus* (R121) Cas13, *Rhodobacter capsulatus* (DE442 Cas13 C2c2, *Leptotrichia wadei* (Lw2) Cas13, or *Listeria seeligeri* Cas13. In some instances, the Cas protein may be a C2 Cas13 c2 ortholog of an organism of a genus which includes but is not limited to *Leptotrichia, Listeria, Corynebacter, Sutterella, Legionella, Treponema, Filifactor, Eubacterium, Streptococcus, Lactobacillus, Mycoplasma, Bacteroides, Flaviivola, Flavobacterium, Sphaerochaeta, Azospirillum, Gluconacetobacter, Neisseria, Roseburia, Parvibaculum, Staphylococcus, Nitratifractor, Mycoplasma* and *Campylobacter*. In other instances, the Cas protein is a chimeric protein comprising fragments from two or more Cas proteins. For example, the Cas protein may comprise fragments of Cas protein orthologs from an organism including, but not limited to, *Leptotrichia, Listeria, Corynebacter, Sutterella, Legionella, Treponema, Filifactor, Eubacterium, Streptococcus, Lactobacillus, Mycoplasma, Bacteroides, Flaviivola, Flavobacterium*, Sphaerochaeta, Azospirillum, *Gluconacetobacter, Neisseria, Roseburia, Parvibaculum, Staphylococcus, Nitratifractor, Mycoplasma* and *Campylobacter*. In other instances, the Cas protein may comprise fragments of Cas protein orthologs of different organism species. Detailed descriptions of Cas proteins that are useful in the present invention and Cas-based diagnostic assays can be found, e.g., in, WO2019/148206, WO2019/126577, WO2019/071051, WO2019/051318, WO2018/107129, WO2018/170340, Gootenberg et al., *Science*, 2017, 356: 438-442, Gootenberg et al., *Science*, 2018, 360(6387): 439-444, and Chen et al., *Science*, 2018, 360(6387): 436-439, the contents in their entirety are herein incorporated by reference.

In some embodiments, the Cas protein is bound to a solid substrate. In certain embodiments, the Cas protein is immobilized on a solid substrate in an individual sample reaction nanostructure. In some embodiments, the solid support comprises a patterned surface suitable for immobilization of molecules in an ordered pattern or arrayed pattern. In certain embodiments, a patterned surface refers to an arrangement of different regions in or on an exposed layer of a solid support. In some embodiments, the solid support comprises an array of wells or depressions in a surface. The composition and geometry of the solid support can vary with its use. A biological sample containing, or suspected of containing, the target nucleic acids may then be exposed to the substrate to allow binding of the target nucleic acids to the bound Cas protein.

C. Guide Sequences

The term "CRISPR targeting RNA," "crRNA," "guide RNA," or "single guide RNA," or "gRNA" refers to a polynucleotide comprising any polynucleotide sequence having sufficient complementarity with a target nucleic acid sequence to hybridize with the target nucleic acid sequence (e.g., target DNA sequence and target RNA sequence) and to direct sequence-specific binding of a CRISPR complex comprising the guide sequence and a Cas protein to the target nucleic acid sequence.

In some embodiments, the percentage of complementarity of the guide sequence and the target nucleic acid sequence (e.g., target DNA sequence and target RNA sequence), when optimally aligned using a suitable alignment algorithm, is at least about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g., the Burrows Wheeler Aligner), ClustalW, Clustal X, BLAT, Novoalign (Novocraft Technologies), ELAND (Illumina, San Diego, Calif.), SOAP, and Maq.

A guide sequence may be selected to target any target nucleic acid sequence. In some embodiments, a guide sequence is at least about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. In various embodiments, the guide sequence is 10-30 nucleotides long.

The ability of a guide sequence to direct sequence-specific binding of a CRISPR complex to a target nucleic acid sequence may be assessed by any suitable assay known to those skilled in the art. For example, the components of a CRISPR system sufficient to form a CRISPR complex, including the guide sequence to be tested, may be provided to a host cell having the corresponding target nucleic acid sequence, such as by transfection with vectors encoding the components of the CRISPR complex, followed by an assessment of preferential targeting (e.g., cleavage) within the target nucleic acid sequence. Similarly, cleavage of a target nucleic acid sequence may be evaluated in a test tube by providing the target nucleic acid sequence, components of a CRISPR complex, including the guide sequence to be tested and a control guide sequence different from the test guide sequence, and comparing binding or rate of cleavage at the target sequence between the test and control guide sequence reactions. The CRISPR system of the present invention utilizes guide sequences compatible with the Cas protein employed. In some embodiments, the guide sequence (e.g., gRNA) comprises a crRNA. In other embodiments, the guide sequence comprises a crRNA and a trans-activating crRNA(tracrRNA).

In some embodiments, a guide sequence is selected to reduce the degree of secondary structure within the sequence. In some embodiments, about or less than about 75%, 50%, 40%, 30%, 25%, 20%, 15%, 10%, 5%, 1%, or fewer of the nucleotides of the guide sequence participate in self-complementary base pairing when optimally folded. Optimal folding may be determined by any suitable polynucleotide folding algorithm.

In some embodiments, guide sequences comprise non-naturally occurring nucleic acids and/or non-naturally occurring nucleotides and/or nucleotide analogs, and/or chemical modifications. Non-naturally occurring nucleic acids can include, for example, mixtures of naturally and non-naturally occurring nucleotides. Non-naturally occurring nucleotides and/or nucleotide analogs may be modified at the ribose, phosphate, and/or base moiety. In certain embodiments, a guide nucleic acid comprises ribonucleotides and non-ribonucleotides. In some embodiments, a guide nucleic acid comprises one or more ribonucleotides and one or more deoxyribonucleotides. In some embodiments, a guide nucleic acid comprises one or more non-naturally occurring nucleotide or nucleotide analog such as a nucleotide with phosphorothioate linkage, boranophosphate linkage, a locked nucleic acid (LNA) nucleotides comprising a methylene bridge between the 2' and 4' carbons of the ribose ring, or bridged nucleic acids (BNA). Other useful modified nucleotide and chemical modifications are described in WO2018/107129.

In some embodiments, the guide sequence of the assay is specific to one or more target sequences selected from the group consisting of P53, PIK3CA, MAP3KI, MAP2K4, PIK3R1, LPA, KRAS, ERBB2, FGFR2, and TNXB. As such, a guide sequence is selected to direct the CRISPR complex to P53, PIK3CA, MAP3KI, MAP2K4, PIK3R1, LPA, KRAS, ERBB2, FGFR2, or TNXB. In some embodiments, the guide sequence is specific to a particular mutation of P53. In some embodiments, the guide sequence is specific to a particular mutation of PIK3CA. In some embodiments, the guide sequence is specific to a particular mutation of P53. In some embodiments, the guide sequence is specific to a particular mutation of MAP3KI. In some embodiments, the guide sequence is specific to a particular mutation of MAP2K4. In some embodiments, the guide sequence is specific to a particular mutation of PIK3R1. In some embodiments, the guide sequence is specific to a particular mutation of LPA. In some embodiments, the guide sequence is specific to a particular mutation of KRAS. In some embodiments, the guide sequence is specific to a particular mutation of ERBB2. In some embodiments, the guide sequence is specific to a particular mutation of FGFR2. In some embodiments, the guide sequence is specific to a particular mutation of TNXB.

In some embodiments, the guide sequence of the assay is specific to one or more target sequences selected from the group consisting of AKT1, BRAF, EGFR, KRAS, MAP2K1, NRAS, PI3KCA, and PTEN. As such, a guide sequence is selected to direct the CRISPR complex to AKT1, BRAF, EGFR, KRAS, MAP2K1, NRAS, PI3KCA, and PTEN.

In some embodiments, the guide sequence is attached on a solid substrate in an individual sample reaction nanostructure. Any known method can be employed to immobilize a nucleic acid sequence to the substrate, including, but not limited to, lithography, photolithography, photoelectrochemical synthesis, bead array assembly, and the like. In some embodiments, the Cas protein is linked to streptavidin and functionalized to the surface with a spacer molecule and biotin at one end.

D. Non-Specific Nucleic Acid Reporters

A non-specific nucleic acid reporter of the invention comprises an RNA element that is cleavable by an active Cas protein. In some embodiments, cleavage of the RNA element releases agents or a detectable signal. In some embodiments, cleavage of the RNA element produces conformational changes that allow a detectable signal to be produced. However, prior to cleavage, a detectable signal is not produced. A positive detectable signal may be any signal that can be detected using optical, fluorescent, chemiluminescent, electrochemical or other detection methods known in the art.

In some embodiments, the non-specific nucleic acid reporter comprises a quencher/fluorophore pair, e.g., a quencher moiety and a fluorescent moiety. Upon cleavage of the nucleic acid reporter by an active Cas protein, the quencher moiety no longer quenches the fluorescent signal of the fluorescent moiety and the fluorescent signal can be detected. In some instances, the fluorophore and quencher of the reporter are in sufficient proximity for contact quenching to occur.

In some embodiments, the non-specific nucleic acid reporter is immobilized on a solid substrate in an individual sample reaction nanostructure. In certain embodiments, the solid substrate is a nanostructure. In certain embodiments, the solid substrate is a bead. Any known method can be employed to immobilize the non-specific nucleic acid reporter to the substrate, including, but not limited to, lithography, photolithography, photo-electrochemical synthesis, bead array assembly, and the like.

IV. CTC-Based Devices and Assays

Provided herein are devices (e.g., diagnostic devices) and methods for in vivo screening of circulating tumor cells (CTCs) in a subject to determine if the subject has or is likely to have a cancer condition. CTCs can appear in early stages of cancer and can be found during tumor progression and metastatic cancer. In some embodiments, the devices and method presented herein can be used for determining cancer prognosis, monitoring cancer recurrence, monitoring therapeutic response, evaluating drug resistance, and a combination thereof by detecting CTCs.

A. Circulating Tumor Cells

The needle portion of an in vivo diagnostic device described can be inserted into a blood vessel of the subject to contact CTCs. In some embodiments, CTCs are separated from the circulating blood by way of size or other physical or biophysical properties of the cells. In some instances, separation occurs using openings (e.g., pores or holes) or three-dimensional geometries present on the device, e.g., the needle. In some embodiments, CTCs contact the surface of the needle body without local enrichment of the cells.

The detection of specific CTCs can indicate that a patient has a cancer condition including, but not limited to, breast cancer, lung cancer, prostate cancer, colorectal cancer, renal cancer, uterine cancer, pancreatic cancer, cancer of the esophagus, a lymphoma, head/neck cancer, ovarian cancer, a hepatobiliary cancer, a melanoma, cervical cancer, multiple myeloma, leukemia, thyroid cancer, bladder cancer, and gastric cancer. In some embodiments, the cancer condition is a predefined subtype of a cancer, an early stage cancer, or a late stage cancer.

In some embodiments, the cancer condition is selected from the group consisting of a predefined stage of a breast cancer, a predefined stage of a lung cancer, a predefined stage of a prostate cancer, a predefined stage of a colorectal cancer, a predefined stage of a renal cancer, a predefined stage of a uterine cancer, a predefined stage of a pancreatic cancer, a predefined stage of a cancer of the esophagus, a predefined stage of a lymphoma, a predefined stage of a head/neck cancer, a predefined stage of a ovarian cancer, a predefined stage of a hepatobiliary cancer, a predefined stage of a melanoma, a predefined stage of a cervical cancer, a predefined stage of a multiple myeloma, a predefined stage of a leukemia, a predefined stage of a thyroid cancer, a predefined stage of a bladder cancer, and a predefined stage of a gastric cancer.

In some embodiments, CTCs of a particular cancer condition express one or more specific target molecules on their cell surface which can be detected using the devices and methods described herein.

B. Target Binding Molecules

CTCs in contact with the device can contact (e.g., bind to) the sample reaction nanostructures of the surface of the needle body. In some embodiments, the sample reaction nanostructure comprises a target binding molecule that binds to a specific target molecule on the surface of the CTC. In some embodiments, the target binding molecule is an antibody or an antibody variant (e.g., an antibody that differs from a parental antibody by at least one amino acid modification). Non-limiting examples of an antibody variant include antibody derivatives, fragments, mimetics, and the like. In some embodiments, the antibody comprises a single-chain variable fragment (scFv) that binds the target molecule. In some embodiments, the antibody comprises an antigen-binding fragment (e.g., Fab) that binds the target molecule.

In some embodiments, the CTC-based device comprises a plurality of sample reaction nanostructures. In some instances, the plurality of sample reaction nanostructures comprises for assaying one or more target molecule. In some embodiments, the device is formatted to detect one or more target molecules, e.g., 1, 2, 3, 4, 5, 6, 7, 8, 9 or 10 different target molecules.

In some embodiments, each sample reaction nanostructure comprises at least one target binding molecule. In some embodiments, each sample reaction nanostructure comprises at least two different target binding molecules. The two different targeting binding molecules may bind the same target molecule. In other instances, the two different targeting binding molecules may bind different target molecules. In particular cases, two sample reaction nanostructures can include one or more different target binding molecules. In other cases, two sample reaction nanostructures of the needle include the same target binding molecules.

The target binding molecule can be bound directly or indirectly to the surface of the needle body. In some embodiments, the target binding molecule is immobilized, cross-linked, or functionalized onto the surface. In certain embodiments, the target binding molecule is deposited on a material, e.g., nanomaterial to produce an immunosensor that can signal binding of the target binding molecule to the target molecule.

In some embodiments, the target molecule on the CTC is a cancer- or tumor-associated cell surface antigen. In some embodiments, the target molecule is epithelial cell adhesion molecule (EPCAM), prostate-specific membrane protein (PSMA), human epidermal growth factor receptor (HER2), or any combination thereof. In some embodiments, the CTC-based device comprises sample reaction nanostructures for detecting those selected from the group consisting of EPCAM, PSMA, HER2, EPCAM/PSMA, EPCAM/HER2, PSMA/HER2, and EPCAM/PSMA/HER2.

As used herein, the term "EPCAM" refers to an EPCAM protein, an EPCAM polypeptide having substantially the same amino acid sequence as the EPCAM protein, or a fragment thereof such as an immunoreactive fragment thereof. An EPCAM polypeptide generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with an EPCAM protein, with the amino acid identity determined using a sequence alignment program such as CLUSTALW. The amino acid sequence of human EPCAM can be found, for example, as NCBI Ref. Seq. NP_002345.2 or Uniprot No. P16422. The term "EPCAM" can be used interchangeably with any one of the terms "DIAR5," "EGP-2," "EGP314," "EGP40," "ESA," "HNPCC8," "KS1/4," "KSA," "M4S1," "MIC18," "MK-1," "TACSTD1," and "TROP1."

As used herein, the term "PSMA" refers to a PSMA protein, a PSMA polypeptide having substantially the same amino acid sequence as the PSMA protein, or a fragment thereof such as an immunoreactive fragment thereof. A PSMA polypeptide generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with a PSMA protein, with the amino acid identity determined using a sequence alignment program such as CLUSTALW. The amino acid sequence of human PSMA can be found, for example, as NCBI Ref. Seqs. NP_004467.1, NP_001014986.1, NP_001180400.1, NP_001180401.1, NP_001180402.1, or Uniprot No. Q04609. The term "PSMA" can be used interchangeably with any one of the terms "glutamate carboxypeptidase 2," "GCPII," "folate hydrolase 1," "FOLH1," "N-acetyl-L-aspartyl-L-glutamate peptidase I," "NAALADase I," and "NAAG peptidase."

As used herein, the term "HER2" refers to a HER2 protein, a HER2 polypeptide having substantially the same amino acid sequence as the HER2 protein, or a fragment thereof such as an immunoreactive fragment thereof. A HER2 polypeptide generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with a HER2 protein, with the amino acid identity determined using a sequence alignment program such as CLUSTALW. The amino acid sequence of human HER2 can be found, for example, as NCBI Ref. Seqs. NP_001005862.1, NP_001276865.1, NP_001276866.1, NP_001276867.1, NP_004439.2, or Uniprot No. P04626. The term "HER2" can be used interchangeably with any one of the terms "ERBB2," "MLN19," "NEU," "NGL," "TKR1," "receptor tyrosine protein kinase erbB-2," "metastatic lymph node gene 19 protein," "proto-oncogene c-ERBB-2," "tyrosine kinase-type cell surface receptor HER2," "p185erbB2," "CD340," "human epidermal growth factor receptor 2," and "HER2/neu."

The target binding molecules can be located in the sample reaction nanostructures on needle. In some embodiments, at least one target binding molecule, such as but not limited to, at least one antibody is deposited at a particular addressable position on the surface of the needle. In some instances, an antibody against EPCAM, an antibody against PSMA, or an antibody against HER2 is located in the reaction nanostructure. In other embodiments, two or more targeting binding molecules are deposited in a sample reaction nanostructure. The two or more targeting binding molecules can bind the same target molecule. In certain cases, the two or more targeting binding molecules can bind different target molecules. In other words, a first antibody against first target molecule and a second antibody against second target molecule can be located in the nanostructure.

To detect binding of the target binding molecule to the CTC, an antibody reporter can be used in the sample reaction nanostructure. In some embodiments, the antibody reporter comprises an antibody and a reporter molecule such as a detectable moiety, e.g., a fluorescent moiety, chemilluminescent moiety, optical moiety, and the like. In some embodiments, the antibody reporter comprises an antibody that bind a targeting binding molecule. In other embodiments, the antibody reporter comprises an antibody that bind a second target molecule that is different than the first target molecule. In some embodiments, the diagnostic device can include: an antibody against EPCAM and an antibody PSMA; an antibody against EPCAM and an antibody HER2; an antibody against PSMA and an antibody HER2; or an antibody against EPCAM, an antibody against PSMA, and an antibody HER2.

V. Exemplary Deposition Techniques

A. Deposition Methods

The following subsections describe individual fabrication techniques that can be used to deposit layers of material, hereinafter referred to collectively as "deposit materials," in order to form some or all of the layers of the nanostructures 202 of some embodiments of the present disclosure. The techniques disclosed below generally are used to prepare a noncontiguous substrate region for each nanostructure 202 on a surface of a needle. However, the techniques may also be used to form additional layers or components of each nanostructure 202 on an application dependent basis.

Chemical Vapor Deposition.

In some embodiments, one or more layers of the deposit materials are deposited by chemical vapor deposition. In chemical vapor deposition (CVD), the constituents of a vapor phase, often diluted with an inert carrier gas, react at a hot surface (typically higher than 190° C.) to deposit a solid film. Generally, chemical vapor deposition reactions require the addition of energy to the system, such as heating the chamber or the needle substrate. For more information on chemical vapor deposition, exemplary devices used to perform chemical vapor deposition, and process conditions are used to perform chemical vapor deposition of silicon nitride, see Van Zant, *Microchip Fabrication*, Fourth Edition, McGraw-Hill, New York, 2000, pp. 363-393; and Madou, *Fundamentals of Microfabrication*, Second Edition, 2002, pp. 144-154, CRC Press, each of which are hereby incorporated by reference herein in their entireties.

*Reduced Pressure Chemical Vapor Deposition.* In some embodiments, one or more layers of the deposit materials are deposited by reduced pressure chemical vapor deposition (RPCVD). RPCVD is typically performed at below 10 Pa and at temperatures in the range of (550° C.–600° C.). The low pressure used in RPCVD results in a large diffusion coefficient, which leads to growth of a layer that is limited by the rate of surface reactions rather than the rate of mass transfer to the substrate. In RPCVD, reactants can typically be used without dilution. RPCVD is performed, for example, in some embodiments, in a horizontal tube hot wall reactor.

*Low Pressure Chemical Vapor Deposition.* In some embodiments, one or more layers of the deposit materials are deposited by low pressure chemical vapor deposition (LPCVD) or very low pressure CVD. LPCVD is typically performed at below 1 Pa.

Atmospheric Chemical Vapor Deposition. In some embodiments, one or more layers of the deposit materials are deposited by atmospheric to slightly reduced pressure chemical vapor deposition. Atmospheric pressure to slightly reduced pressure CVD (APCVD) is used, for example, to grow APCVD is a relatively simplistic process that has the advantage of producing layers at high deposition rates and low temperatures (350° C.-400° C.).

Plasma Enhanced Chemical Vapor Deposition.

In some embodiments, one or more layers of the deposit materials are deposited by plasma enhanced (plasma assisted) chemical vapor deposition (PECVD). PECVD systems feature a parallel plate chamber operated at a low pressure (e.g., 2-5 Torr) and low temperature (300° C.–400° C.). A radio-frequency-induced glow discharge, or other plasma source is used to induce a plasma field in the deposition gas. PECVD systems that are used include, but are not limited to, horizontal vertical flow PECVD, barrel radiant-heated PECVD, and horizontal-tube PECVD. In some embodiments, remote plasma CVD (RPCVD) is used. Remote plasma CVD is described, for example, in U.S. Pat. No. 6,458,715 to Sano et al., which is hereby incorporated by reference in its entirety.

Anodization.

In some embodiments, one or more layers of the deposit materials are deposited by anodization. Anodization is an oxidation process performed in an electrolytic cell. The material to be anodized becomes the anode (+) while a noble metal is the cathode (−). Depending on the solubility of the anodic reaction products, an insoluble layer (e.g., an oxide) results. If the primary oxidizing agent is water, the resulting oxides generally are porous, whereas organic electrolytes lead to very dense oxides providing excellent passivation. See, e.g., Madou et al., 1982, J. Electrochem. Soc. 129, pp. 2749-2752, which is hereby incorporated by reference in its entirety.

Sol-Gel Deposition Techniques.

Figure 2:
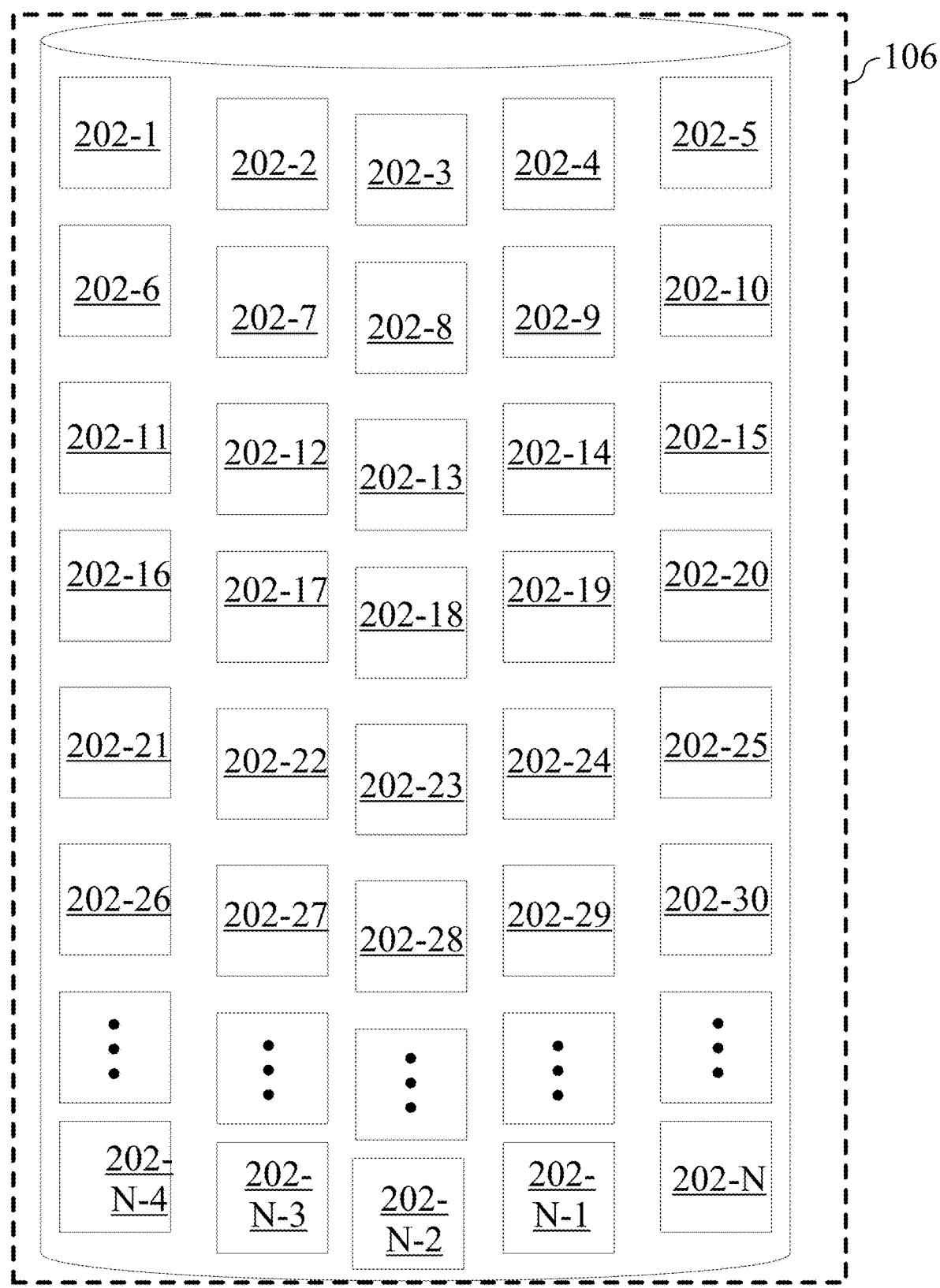
FIG. 2 provides a close-up diagram of the addressable, patterned plurality of sample reaction nanostructures 106 (Exemplary sample reaction nanostructures are depicted as 202-1 to 202-30, and 202-N to 202-N-4.

In some embodiments, one or more layers of the deposit materials are deposited by a sol-gel process. In a sol-gel process solid particles, chemical precursors, in a colloidal suspension in a liquid (a sol) forms a gelatinous network (a gel). Upon removal of the solvent by heating a glass or ceramic layer. Both sol and gel formation are low-temperature processes. For sol formation, an appropriate chemical precursor is dissolved in a liquid, for example, tetraethylsiloxane (TEOS) in water. The sol is then brought to its gel-point, that is, the point in the phase diagram where the sol abruptly changes from a viscous liquid to a gelatinous, polymerized network. In the gel state the material is shaped (e.g., a fiber or a lens) or applied onto a substrate (e.g., the needle 104 illustrated in FIG. 1 and in enlarged form in FIG. 2) by spinning, dipping, or spraying. In the case of TEOS, a silica gel is formed by hydrolysis and condensation using hydrochloric acid as the catalyst. Drying and sintering at temperatures between 200° C. to 600° C. transforms the gel into a glass and ultimately into silicon dioxide.

Plasma Spraying Techniques.

In some embodiments, one or more layers of the deposit materials are deposited by a plasma spraying process. With plasma spraying, almost any material can be coated on many types of substrates. Plasma spraying is a particle deposition method. Particles, a few microns to 100 microns in diameter, are transported from source to substrate. In plasma spraying, a high-intensity plasma arc is operated between a sticktype cathode and a nozzle-shaped water-cooled anode. Plasma gas, pneumatically fed along the cathode, is heated by the arc to plasma temperatures, leaving the anode nozzle as a plasma jet or plasma flame. Argon and mixtures of argon with other noble (He) or molecular gases ($H_2$, $N_2$, $O_2$, etc.) are frequently used for plasma spraying. Fine powder suspended in a carrier gas is injected into the plasma jet where the particles are accelerated and heated. The plasma jet reaches temperatures of 20,000 K and velocities up to 1000 $ms_{-1}$ in some embodiments. The temperature of the particle surface is lower than the plasma temperature, and the dwelling time in the plasma gas is very short. The lower surface temperature and short duration prevent the spray particles from being vaporized in the gas plasma. The particles in the plasma assume a negative charge, owing to the different thermal velocities of electrons and ions. As the molten particles splatter with high velocities onto a substrate, they spread, freeze, and form a more or less dense coating, typically forming a good bond with the substrate. Plasma spraying equipment is available from Sulzer Metco (Winterthur Switzerland). For more information on plasma spraying, see, for example, Madou, *Fundamentals of Microfabrication*, Second Edition, 2002, pp. 157-159, CRC Press, which is hereby incorporated by reference in its entirety.

Ink Jet Printing.

In some embodiments, one or more layers of the deposit materials are deposited by ink-jet printing. Ink jet printing is based on the same principles of commercial ink-jet printing. The ink jetnozzle is connected to a reservoir filled with the chemical solution and placed above a computer-controlled x-y stage. The target object is placed on the x-y stage and, under computer control, liquid drops (e.g., 50 microns in diameter) are expelled through the nozzle onto a well-defined place on the object. Different nozzles print different spots in parallel. In one embodiment of the present disclosure, a bubble jet, with drops as small as a few picoliters, is used to form a layer of a deposit material. In another embodiment, a thermal ink jet (Hewlett Packard, Palo Alto, Calif.) is used to form a layer of a deposit material. In a thermal ink jet, resistors are used to rapidly heat a thin layer of liquid ink. A superheated vapor explosion vaporizes a tiny fraction of the ink to form an expanding bubble that ejects a drop of ink from the ink cartridge onto the substrate. In still another embodiment of the present disclosure, a piezoelectric ink jethead is used for ink-jet printing. A piezoelectric ink-jet head includes a reservoir with an inlet port and a nozzle at the other end. One wall of the reservoir consists of a thin diaphragm with an attached piezoelectric crystal. When voltage is applied to the crystal, it contracts laterally, thus deflecting the diaphragm and ejecting a small drop of fluid from the nozzle. The reservoir then refills via capillary action through the inlet. One, and only one, drop is ejected for each voltage pulse applied to the crystal, thus allowing complete control over the when a drop is ejected. In yet another embodiment of the present disclosure, an epoxy delivery system is used to deposit a layer of a reaction nanostructure 202. An example of an epoxy delivery system is the Ivek Digispense 2000 (Ivek Corporation, North Springfield, Vt.). For more information on jet spraying, see, for example, Madou, *Fundamentals of Microfabrication*, Second Edition, 2002, pp. 164-167, CRC Press, which is hereby incorporated by reference herein in its entirety.

Vacuum Evaporation.

In one embodiment of the present disclosure, one or more layers of the deposit materials are deposited by vacuum evaporation. Vacuum evaporation takes place inside an evacuated chamber. The chamber can be, for example, a quartz bell jar or a stainless steel enclosure. Inside the chamber is a mechanism that evaporates the metal source, a wafer holder, a shutter, thickness and rate monitors, and heaters. The chamber is connected to a vacuum pump. There are any number of different ways in which the metal is evaporated within the chamber, including filament evaporation, E-beam gun evaporation, and hot plate evaporation. See, for example, Van Zant, *Microchip Fabrication*, Fourth Edition, McGraw-Hill, New York, 2000, pp. 407-411, which is hereby incorporated by reference herein in its entirety.

Sputter Deposition/Physical Vapor Deposition.

In another embodiment of the present disclosure, one or more layers of the deposit materials are deposited by sputtering. Sputtering, like evaporation, takes place in a vacuum. However, it is a physical not a chemical process (evaporation is a chemical process), and is referred to as physical vapor deposition. Inside the vacuum chamber is a slab, called a target, of the desired film material. The target is electrically grounded. An inert gas such as argon is introduced into the chamber and is ionized to a positive charge. The positively charged argon atoms are attracted to the grounded target and accelerate toward it. During the acceleration they gain momentum, and strike the target, causing target atoms to scatter. That is, the argon atoms "knock off" atoms and molecules from the target into the chamber. The sputtered atoms or molecules scatter in the chamber with some coming to rest on the wafer. A principal feature of a sputtering process is that the target material is deposited on the wafer with chemical or compositional change. In some embodiments of the present disclosure, direct current (DC) diode sputtering, radio frequency (RF) diode sputtering, triode sputtering, DC magnetron sputtering or RF magnetron sputtering is used. See, for example, Van Zant, *Microchip Fabrication*, Fourth Edition, McGraw-Hill, New York, 2000, pp. 411-415; U.S. Pat. Nos. 5,203,977; 5,486,277; and 5,742,471, each of which is hereby incorporated by reference herein in its entirety.

RF diode sputtering is a vacuum coating process where an electrically isolated cathode is mounted in a chamber that can be evacuated and partially filled with an inert gas. If the cathode material is an electrical conductor, a direct-current high-voltage power supply is used to apply the high voltage potential. If the cathode is an electrical insulator, the polarity of the electrodes is reversed at very high frequencies to prevent the formation of a positive charge on the cathode that would stop the ion bombardment process. Since the electrode polarity is reversed at a radio frequency, this process is referred to as I33 sputtering. Magnetron sputtering is different form of sputtering. Magnetron sputtering uses a magnetic field to trap electrons in a region near the target surface thus creating a higher probability of ionizing a gas atom. The high density of ions created near the target surface causes material to be removed many times faster than in diode sputtering. The magnetron effect is created by an array of permanent magnets included within the cathode assembly that produce a magnetic field normal to the electric field.

Collimated Sputtering.

In another embodiment of the present disclosure, one or more layers of the deposit materials are deposited by collimated sputtering. Collimated sputtering is a sputtering process where the arrival of metal occurs at an angel normal to the wafer surface. The metal is collimated by a thick honeycomb grid that effectively blocks off angle metal atoms in some embodiments. Alternatively, ionizing the metal atoms and attracting them towards the needle substrate collimates the metal. Collimated sputtering improves filling of high aspect ratio contacts.

Laser Ablated Deposition.

In another embodiment of the present disclosure, one or more layers of the deposit materials are deposited by laser ablated deposition. In one form of laser ablated deposition, a rotating cylindrical target surface is provided for the laser ablation process. The target is mounted in a vacuum chamber so that it is rotated about the longitudinal axis of the cylindrical surface target and simultaneously translated along the longitudinal axis. A laser beam is focused by a cylindrical lens onto the target surface along a line that is at an angle with respect to the longitudinal axis to spread a plume of ablated material over a radial arc. The plume is spread in the longitudinal direction by providing a concave or convex lateral target surface. The angle of incidence of the focused laser beam is other than normal to the target surface to provide a glancing geometry in some embodiments. Simultaneous rotation about and translation along the longitudinal axis produce a smooth and even ablation of the entire cylindrical target surface and a steady evaporation plume. Maintaining a smooth target surface is useful in reducing undesirable splashing of particulates during the laser ablation process and thereby depositing high quality thin films. See, for example, U.S. Pat. No. 5,049,405, which is hereby incorporated by reference herein in its entirety.

Molecular Beam Deposition.

In another embodiment of the present disclosure, one or more layers of the deposit materials are deposited by molecular beam deposition. Molecular beam deposition is a method of growing films, under vacuum conditions, by directing one or more molecular beams at a substrate. In some instances, molecular beam deposition involves epitaxial film growth on single crystal substrates by a process that typically involves either the reaction of one or more molecular beams with the substrate or the deposition on the substrate of the beam particles. The term "molecular beam" refers to beams of monoatomic species as well as polyatomic species. The term molecular beam deposition includes both epitaxial growth and nonepitaxial growth processes. Molecular beam deposition is a variation of simple vacuum evaporation. However, molecular beam deposition offers better control over the species incident on the substrate than does vacuum evaporation. Good control over the incident species, coupled with the slow growth rates that are possible, permits the growth of thin layers having compositions (including dopant concentrations) that are precisely defined. Compositional control is aided by the fact that growth is generally at relatively low substrate temperatures, as compared to other growth techniques such as liquid phase epitaxy or chemical vapor deposition, and diffusion processes are very slow.

Essentially arbitrary layer compositions and doping profiles are obtained with precisely controlled layer thickness. In fact, layers as thin as a monolayer are grown by MBE.

Furthermore, the relatively low growth temperature permits growth of materials and use of substrate materials that could not be used with higher temperature growth techniques. See for example, U.S. Pat. No. 4,681,773, which is hereby incorporated by reference herein in its entirety.

Ionized Physical Vapor Deposition.

In another embodiment of the present disclosure, one or more layers of the deposit materials are deposited by ionized physical vapor deposition (I-PVD), also known as ionized metal plasma (IMP). In I-PVD, metal atoms are ionized in an intense plasma. Once ionized, the metal is directed by electric fields perpendicular to the needle body surface. Metal atoms are introduced into the plasma by sputtering from the target. A high density plasma is generated in the central volume of the reactor by an inductively coupled plasma (ICP) source. This electron density is sufficient to ionize approximately 80% of the metal atoms incident at the wafer surface. The ions from the plasma are accelerated and collimated at the surface of the wafer by a plasma sheath. The sheath is a region of intense electric field that is directed toward the wafer surface. The field strength is controlled by applying a radio frequency bias.

Ion Beam Deposition.

In another embodiment of the present disclosure, one or more layers of the deposit materials are deposited by ion beam deposition (IBD). IBD uses an energetic, broad beam ion source carefully focused on a grounded metallic or dielectric sputtering target. Material sputtered from the target deposits on a nearby substrate to create a film. Most applications also use a second ion source, termed an ion assist source (IAD), which is directed at the substrate to deliver energetic noble or reactive ions at the surface of the growing film. The ion sources are "gridded" ion sources and are typically neutralized with an independent electron source. IBD processing yields excellent control and repeatability of film thickness and properties. Process pressures in IBD systems are approximately $10^{-4}$ Torr. Hence, there is very little scattering of either ions delivered by the ion sources or material sputtered from the target of the surface. Compared to sputter deposition using magnetron or diode systems, sputter deposition by IBD is highly directional and more energetic. In combination with a substrate fixture that rotates and changes angle, IBD systems deliver a broad range of control over sidewall coatings, trench filling and liftoff profiles.

Atomic Layer Deposition.

In another embodiment of the present disclosure, one or more layers of the deposit materials are deposited by atomic layer deposition. Atomic layer deposition is also known as atomic layer epitaxy, sequential layer deposition, and pulsed-gas chemical vapor deposition. Atomic layer deposition involves use of a precursor based on self-limiting surface reactions. Generally, an object is exposed to a first species that deposits as a monolayer on the object. Then, the monolayer is exposed to a second species to form a fully reacted layer plus gaseous byproducts. The process is typically repeated until a desired thickness is achieved. Atomic layer deposition and various methods to carry out the same are described in U.S. Pat. No. 4,058,430 to Suntola et al., entitled "Method for Producing Compound Thin Films," U.S. Pat. No. 4,413,022 to Suntola et al., entitled "Method for Performing Growth of Compound Thin Films," to Ylilammi, and George et al., 1996, J. Phys. Chem. 100, pp. 13121-13131, each of which is hereby incorporated by reference herein in its entirety. Atomic layer deposition has also been described as a chemical vapor deposition operation performed under controlled conditions that cause the deposition to be self-limiting to yield deposition of, at most, a monolayer. The deposition of a monolayer provides precise control of film thickness and improved compound material layer uniformity. Atomic layer deposition is performed using equipment such as the Endura Integrated Cu Barrier/Seed system (Applied Materials, Santa Clara, Calif.).

Hot Filament Chemical Vapor Deposition.

In another embodiment of the present disclosure, one or more layers of the deposit materials are deposited by hot filament chemical vapor deposition (HFCVD). In HFCVD, reactant gases are flowed over a heated filament to form precursor species that subsequently impinge on the substrate surface, resulting in the deposition of high quality films. HFCVD has been used to grow a wide variety of films, including diamond, boron nitride, aluminum nitride, titanium nitride, boron carbide, as well as amorphous silicon nitride. See, for example, Deshpande et al., 1995, J. Appl. Phys. 77, pp. 6534-6541, which is hereby incorporated by reference herein in its entirety.

Screen Printing.

In another embodiment of the present disclosure, one or more layers of the deposit materials are deposited by a screen printing (also known as silk-screening) process. A paste or ink is pressed onto portions of an underlying structure through openings in the emulsion on a screen. See, for example, Lambrechts and Sansen, *Biosensors: Microelectrochemical Devices*, The Institute of Physics Publishing, Philadelphia, 1992, which is hereby incorporated by reference in its entirety. The paste consists of a mixture of the material of interest, an organic binder, and a solvent. The organic binder determines the flow properties of the paste. The bonding agent provides adhesion of particles to one another and to the substrate. The active particles make the ink a conductor, a resistor, or an insulator. The lithographic pattern in the screen emulsion is transferred onto portions of the underlying structure by forcing the paste through the mask openings with a squeegee. In a first step, paste is put down on the screen. Then the squeegee lowers and pushes the screen onto the substrate, forcing the paste through openings in the screen during its horizontal motion. During the last step, the screen snaps back, the thick film paste that adheres between the screening frame and the substrate shears, and the printed pattern is formed on the substrate. The resolution of the process depends on the openings in the screen and the nature of the paste. With a 325-mesh screen (i.e., 325 wires per inch or 40 µM holes) and a typical paste, a lateral resolution of 100 µM can be obtained.

For difficult-to-print pastes, a shadow mask, such as a thin metal foil with openings, complements the process. However, the resolution of this method is inferior (>500 µM). After printing, the wet films are allowed to settle for a period of time (e.g., fifteen minutes) to flatten the surface while drying. This removes the solvents from the paste. Subsequent firing burns off the organic binder, metallic particles are reduced or oxidized, and glass particles are sintered. Typical temperatures range from 500° C. to 1000° C. After firing, the thickness of the resulting layer ranges from 10 µM to 50 µM. One silk-screening setup is the DEK 4265 (Universal Instrument Corporation, Binghamton, N.Y.). Commercially available inks (pastes) that can be used in the screen printing include conductive (e.g., Au, Pt, Ag/Pd, etc.), resistive (e.g., $RuO_2$, $IrO_2$), overglaze, and dielectric (e.g., $Al_2O_3$, $ZrO_2$). The conductive pastes are based on metal particles, such as Ag, Pd, Au, or Pt, or a mixture of these combined with glass. Resistive pastes are based on $RuO_2$ or $Bi_2Ru_2O_7$ mixed with glass (e.g., 65% PBO, 25% $SiO_2$, 10% $Bi_2O_3$). The resistivity is determined by the mixing ratio. Overglaze and dielectric pastes are based on glass mixtures. Different melting temperatures can be achieved by adjusting the paste composition. See, for example, Madou, *Fundamentals of Microfabrication*, Second Edition, CRC Press, Boca Raton, Fla., 2002, pp. 154-156, which is hereby incorporated by reference herein in its entirety.

Electroless Metal Deposition.

In another embodiment of the present disclosure, one or more layers of the deposit materials are deposited by electroless metal deposition. In electroless plating a layer is built by chemical means without applying a voltage. Electroless plating baths can be used to form Au, Co—P, Cu, Ni—Co, Ni—P, Pd, or Pt layers. See, for example, Madou, *Fundamentals of Microfabrication*, Second Edition, CRC Press, Boca Raton, Fla., 2002, pp. 344-345, which is hereby incorporated by reference herein in its entirety Electroplating.

In another embodiment of the present disclosure, one or more layers of the deposit materials are deposited by electroplating. Electroplating takes place in an electrolytic cell. The reactions that take place in electroplating involve current flow under an imposed bias. In some embodiments, a layer is deposited as part of a damascene process. See, for example, Madou, *Fundamentals of Microfabrication*, Second Edition, CRC Press, Boca Raton, Fla., 2002, pp. 346-357, which is hereby incorporated herein by reference in its entirety.

VI. Concluding Remarks

The disclosed devices and methods should not be construed as limiting in any way. Instead, the present disclosure is directed toward all novel and nonobvious features and aspects of the various disclosed embodiments, alone and in various combinations and subcombinations with one another. The disclosed devices and methods are not limited to any specific aspect or feature or combination thereof, nor do the disclosed embodiments require that any one or more specific advantages be present or problems be solved. The technologies from any example can be combined with the technologies described in any one or more of the other examples.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

What is claimed is:

1. A diagnostic device comprising a needle having a body comprising a plurality of sample reaction nanostructures disposed on a surface of the body, wherein the respective sample reaction nanostructures of the plurality of sample reaction nanostructures collectively form an array comprising a plurality of elements;
   each respective element of the array is at a spatially addressable position on the surface of the body;
   each respective element of the array is populated with a sample reaction nanostructure in the plurality of sample reaction nanostructures,
   wherein each sample reaction nanostructure in the plurality of sample reaction nanostructures comprises at least one Cas protein and at least one target engineered CRISPR targeting RNA (crRNA) at the corresponding addressable position on the surface of the body.

2. The diagnostic device of claim 1, wherein each sample reaction nanostructure further comprises:
   at least one non-specific nucleic acid reporter comprising:
   (i) a nucleic acid cleavable by the at least one Cas protein; and
   (ii) a fluorophore pair comprising a quencher molecule and a fluorophore, wherein the fluorophore is detectable upon cleavage of the at least one non-specific nucleic acid reporter.

3. The diagnostic device of claim 1, wherein the at least one Cas protein is selected from the group consisting of: Cas12a, Cas13, Csm6, a derivative of Cas12a, a derivative of Cas13, a derivative of Csm6, a variant of Cas12a, a variant of Cas13, and a variant of Csm6.

4. The diagnostic device of claim 1, wherein each of the at least one target engineered CRISPR targeting RNA (crRNA) corresponds to a gene having one or more mutations selected from the group consisting of: TP53, PIK3CA, PTEN, APC, VHL, KRAS, MLL3, MLL2, ARIDIA, PBRM1, NAV3, EGFR, NF1, PIK3R1, CDKN2A, GATA3, RB1, NOTCHI, FBXW7, CTNNB1, DNMT3A, MAP3K1, FLT3, MALATI, TSHZ3, KEAP1, CDH1, ARHGAP35, CTCF, NFE2L2, SETBP1, BAP1, NPM1, RUNX1, NRAS, IDHI, TBX3, MAP2K4, RPL22, STK1 1, CRIPAK, CEBPA, KDM6A, EPHA3, AKT1, STAG2, BRAF, AR, AJUBA, EPPK1, TSHZ2, PIK3CG, SOX9, ATM, CDKN1B, WT1, HGF, KDM5C, PRX, ERBB4, MTOR, TLR4, U2AF1, ARID5B, TET2, ATRX, MLL4, ELF3, BRCA1, LRRK2, POLQ, FOXAI, IDH2, CHEK2, KIT, HISTIHIC, SETD2, PDGFRA, EP300, FGFR2, CCND1, EPHB6, SMAD4, FOXA2, USP9X, BRCA2, NFE2L3, FGFR3, ASXL1, TGFBR2, SOX17, CDKN1A, B4GALT3, SF3B1, TAF1, PPP2R1A, CBFB, ATR, SIN3A, VEZF1, HIST1H2BD, EIF4A2, CDK12, PHF6, SMC1A, PTPN11, ACVR1B, MAPK81P1, H3F3C, NSD1, TBL1XR1, EGR3, ACVR2A, MECOM, LIFR, SMC3, NCOR1, RPL5, SMAD2, SPOP, AXIN2, MIR142, RAD21, ERCC2, CDKN2C, EZH2, and PCBP1.

5. The diagnostic device of claim 1, wherein the surface of the body comprises a non-corrosive metal, a non-corrosive alloy, nanoparticles, a polymer, gold, platinum, an alloy, or a combination thereof.

6. The diagnostic device of claim 1, wherein the body is made of steel and the surface comprises a deposit layer on the body having an average thickness of 50 Angstroms or less.

7. The diagnostic device of claim 1, wherein the plurality of sample reaction nanostructures comprises between 100 nanostructures and 1000 nanostructures.

8. The diagnostic device of claim 1, wherein the body has a length between about 10 mm and about 200 mm or an inner diameter of at least 2 µm.

9. The diagnostic device of claim 1, wherein the plurality of sample reaction nanostructures are located on the outer surface of the body of the needle such that the plurality of sample reaction nanostructures contact a cell-free biological sample in vivo,
   wherein the cell-free biological sample comprises one selected from the group consisting of cell-free nucleic acids, cell-free DNA molecules, and cell-free RNA molecules.

10. The diagnostic device of claim 9, wherein the body of the needle does not contain any openings allowing access of the cell-free biological sample to the lumen of the needle.

11. The diagnostic device of claim 1, further comprising an enrichment module comprising a binding molecule that binds the cell-free biological sample prior to the cell-free biological sample contacting the plurality of sample reaction nanostructures,
   wherein the enrichment module is in fluid contact with the plurality of sample reaction nanostructures.

12. The diagnostic device of claim 1, wherein the plurality of sample reaction nanostructures are located on the luminal surface of the body of the needle such that the plurality of sample reaction nanostructures contact a cell-free biological sample in vivo,
   wherein the cell-free biological sample comprises one selected from the group consisting of cell-free nucleic acids, cell-free DNA molecules, and cell-free RNA molecules.

13. The diagnostic device of claim 1, wherein each sample reaction nanostructure contains a unique biomarker.

14. A method of screening for a disease condition in a subject using the diagnostic device of claim 1, the method comprising:
   (a) inserting the diagnostic device into the bloodstream of the subject such that a cell-free biological sample contacts the plurality of sample reaction nanostructures;
   (b) removing the diagnostic device from the subject after a period of time; and
   (c) analyzing the plurality of sample reaction nanostructures for a signal that is indicative of the disease condition.

15. The method of claim 14, wherein the period of time is for about 1 minute to about 15 minutes.

16. The method of claim 14, wherein the disease condition is selected from the group consisting of: a cancer condition and a mendelian disease.

17. The method of claim 16, wherein the cancer condition is breast cancer, lung cancer, prostate cancer, colorectal cancer, renal cancer, uterine cancer, pancreatic cancer, cancer of the esophagus, a lymphoma, head/neck cancer, ovarian cancer, a hepatobiliary cancer, a melanoma, cervical cancer, multiple myeloma, leukemia, thyroid cancer, bladder cancer, gastric cancer, a predefined stage thereof, or a combination thereof.

18. The method of claim 14, wherein the sample reaction nanostructure comprises:
- at least one non-specific nucleic acid reporter comprising a nucleic acid cleavable by the at east one Cas protein, and
- a fluorophore pair comprising a quencher molecule and a fluorophore, wherein the fluorophore is detectable upon cleavage of the at least one non-specific nucleic acid reporter.

19. The method of claim 14, wherein the at least one Cas protein is selected from the group consisting of: Cas12a, Cas13, Csm6, a derivative of Cas12a, a derivative of Cas13, a derivative of Csm6, a variant of Cas12a, a variant of Cas13, and a variant of Csm6.

20. The method of claim 14, wherein the cell-free biological sample comprises cell-free nucleic acids, cell-free DNA molecules, or cell-free RNA molecules.

21. A method of predicting the likelihood of a subject having a disease condition to respond to a therapy using the diagnostic device of claim 1, the method comprising:
(a) inserting the diagnostic device into the bloodstream of the subject such that a cell-free biological sample contacts the plurality of sample reaction nanostructures;
(b) removing the diagnostic device from the subject after a period of time; and
(c) analyzing the plurality of sample reaction nanostructures for a signal that is indicative of the predicted likelihood of the subject to respond to the therapy.

* * * * *